(12) United States Patent
Ueki et al.

(10) Patent No.: US 8,481,565 B2
(45) Date of Patent: *Jul. 9, 2013

(54) METHOD FOR STABILIZING ANTI-DEMENTIA DRUG

(75) Inventors: Yosuke Ueki, Kakamigahara (JP); Yasuyuki Suzuki, Kakamigahara (JP); Satoshi Fujioka, Kakamigahara (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 281 days.

This patent is subject to a terminal disclaimer.

(21) Appl. No.: 11/793,722

(22) PCT Filed: Dec. 27, 2005

(86) PCT No.: PCT/JP2005/024254
§ 371 (c)(1),
(2), (4) Date: Oct. 11, 2007

(87) PCT Pub. No.: WO2006/070930
PCT Pub. Date: Jul. 6, 2006

(65) Prior Publication Data
US 2008/0213368 A1    Sep. 4, 2008

(30) Foreign Application Priority Data

Dec. 27, 2004  (JP) ................................ 2004-376770
Feb. 18, 2005  (JP) ................................ 2005-041492

(51) Int. Cl.
*A01N 43/42* (2006.01)
*A61K 9/14* (2006.01)

(52) U.S. Cl.
USPC .......................................... 514/319; 424/487

(58) Field of Classification Search
USPC ........................................................ 514/319
See application file for complete search history.

(56) References Cited

U.S. PATENT DOCUMENTS

| | | | |
|---|---|---|---|
| 2,327,996 A | 8/1943 | Burnam |
| 4,708,874 A | 11/1987 | De Haan et al. |
| 4,710,384 A | 12/1987 | Rotman |
| 4,713,248 A | 12/1987 | Kjornaes et al. |
| 4,748,023 A | 5/1988 | Tamas et al. |
| 4,780,318 A | 10/1988 | Appelgren et al. |
| 4,792,452 A | 12/1988 | Howard et al. |
| 4,832,957 A | 5/1989 | Dempski et al. |
| 4,851,232 A | 7/1989 | Urquhart et al. |
| 4,891,223 A | 1/1990 | Ambegaonkar et al. |
| 4,892,742 A | 1/1990 | Shah |
| 4,894,239 A | 1/1990 | Nonomura et al. |
| 4,940,556 A | 7/1990 | MacFarlane et al. |
| 4,968,508 A | 11/1990 | Oren et al. |
| 4,970,075 A | 11/1990 | Oshlack |
| 4,973,469 A | 11/1990 | Mulligan et al. |
| 4,994,279 A | 2/1991 | Aoki et al. |
| 5,008,113 A | 4/1991 | Kokubo et al. |
| 5,011,694 A | 4/1991 | Nuernberg et al. |
| 5,017,613 A | 5/1991 | Aubert et al. |
| 5,028,664 A | 7/1991 | Ohmura et al. |
| 5,035,899 A | 7/1991 | Saeki et al. |
| 5,102,668 A | 4/1992 | Eichel et al. |
| 5,164,193 A | 11/1992 | Okada et al. |
| 5,186,943 A | 2/1993 | Okada et al. |
| 5,202,128 A | 4/1993 | Morella et al. |
| 5,254,347 A | 10/1993 | Samejima et al. |
| 5,266,331 A | 11/1993 | Oshlack et al. |
| 5,356,896 A | 10/1994 | Kabadi et al. |
| 5,378,474 A | 1/1995 | Morella et al. |
| 5,382,601 A | 1/1995 | Nurnberg et al. |
| 5,399,357 A | 3/1995 | Akiyama et al. |
| 5,399,360 A | 3/1995 | Surer et al. |
| 5,500,227 A | 3/1996 | Oshlack et al. |
| 5,508,042 A | 4/1996 | Oshlack et al. |
| 5,536,752 A | 7/1996 | Ducharme et al. |
| 5,549,912 A | 8/1996 | Oshlack et al. |
| 5,637,309 A | 6/1997 | Tajima et al. |
| 5,656,295 A | 8/1997 | Oshlack et al. |
| 5,773,031 A | 6/1998 | Shah et al. |
| 5,780,057 A | 7/1998 | Conte et al. |
| 5,840,332 A | 11/1998 | Lerner et al. |
| 5,846,563 A | 12/1998 | Baichwal |
| 5,902,632 A | 5/1999 | Mehta |
| 5,958,456 A | 9/1999 | Baichwal et al. |
| 5,962,024 A | 10/1999 | Marvola et al. |
| 5,985,864 A | 11/1999 | Imai et al. |
| 6,027,748 A | 2/2000 | Conte et al. |
| 6,036,973 A | 3/2000 | Guittard et al. |

(Continued)

FOREIGN PATENT DOCUMENTS

| | | |
|---|---|---|
| AU | 2006241771 A1 | 11/2006 |
| CA | 2359381 A1 | 7/2000 |

(Continued)

OTHER PUBLICATIONS

Eudragit, Technical Information: Eudragit RL 100, Eudragit RL PO, Eudragit RS 100, and Eudragit RS PO, pp. 1-7 (2011).*

(Continued)

*Primary Examiner* — Patricia A Duffy
*Assistant Examiner* — Dennis J Parad
(74) *Attorney, Agent, or Firm* — Buchanan Ingersoll & Rooney PC

(57) ABSTRACT

The present invention provides a method for stabilizing an anti-dementia drug in a pharmaceutical composition containing the anti-dementia drug and a high molecular weight basic substance by adding a high molecular weight acidic substance to said pharmaceutical composition. Further, the present invention provides a pharmaceutical composition containing an anti-dementia drug and a high molecular weight basic substance in which a high molecular weight acidic substance is contained for stabilizing the anti-dementia drug. Furthermore, the present invention provides a method for manufacturing a pharmaceutical composition which comprises steps wherein a solution or suspension containing a high molecular weight acidic substance is added to a mixture of an anti-dementia drug and a high molecular weight basic substance for the sake of stabilizing the anti-dementia drug.

2 Claims, 1 Drawing Sheet

U.S. PATENT DOCUMENTS

| | | | |
|---|---|---|---|
| 6,037,347 | A | 3/2000 | Schubert et al. |
| 6,096,339 | A | 8/2000 | Ayer et al. |
| 6,136,343 | A | 10/2000 | Baichwal |
| 6,156,340 | A | 12/2000 | Adeyeye et al. |
| 6,194,000 | B1 | 2/2001 | Smith et al. |
| 6,210,710 | B1 | 4/2001 | Skinner |
| 6,217,903 | B1 | 4/2001 | Skinner |
| 6,245,351 | B1 | 6/2001 | Nara et al. |
| 6,251,430 | B1 | 6/2001 | Zhang et al. |
| 6,262,081 | B1 | 7/2001 | Zaczek |
| 6,287,599 | B1 | 9/2001 | Burnside et al. |
| 6,294,192 | B1 | 9/2001 | Patel et al. |
| 6,310,085 | B1 | 10/2001 | Willis |
| 6,340,695 | B1 | 1/2002 | Gervais |
| 6,346,268 | B1 | 2/2002 | Zhang et al. |
| 6,358,525 | B1 | 3/2002 | Guo et al. |
| 6,372,255 | B1 | 4/2002 | Saslawski et al. |
| 6,436,438 | B1 | 8/2002 | Momberger et al. |
| 6,451,339 | B2 | 9/2002 | Patel et al. |
| 6,531,151 | B1 | 3/2003 | Besse |
| 6,531,152 | B1 | 3/2003 | Lerner et al. |
| 6,569,457 | B2 | 5/2003 | Ullah et al. |
| 6,569,463 | B2 | 5/2003 | Patel et al. |
| 6,576,677 | B1 | 6/2003 | Ukai et al. |
| 6,592,901 | B2 | 7/2003 | Durig et al. |
| 6,627,223 | B2 | 9/2003 | Percel et al. |
| 6,632,451 | B2 | 10/2003 | Penhasi et al. |
| 6,632,454 | B2 | 10/2003 | Beckert et al. |
| 6,635,680 | B2 | 10/2003 | Mulye |
| 6,638,534 | B1 | 10/2003 | Ishibashi et al. |
| 6,645,528 | B1 | 11/2003 | Straub et al. |
| 6,660,731 | B2 | 12/2003 | Patel et al. |
| 6,667,060 | B1 | 12/2003 | Vandecruys |
| 6,673,369 | B2 | 1/2004 | Rampal et al. |
| 6,685,962 | B2 | 2/2004 | Friedman et al. |
| 6,692,769 | B1 | 2/2004 | Ishibashi et al. |
| 6,706,283 | B1 | 3/2004 | Appel et al. |
| 6,730,321 | B2 | 5/2004 | Ting et al. |
| 6,734,195 | B2 | 5/2004 | Weisman et al. |
| 6,759,431 | B2 * | 7/2004 | Hunter et al. ............... 514/449 |
| 6,805,881 | B1 | 10/2004 | Kanikanti et al. |
| 6,893,661 | B1 | 5/2005 | Odidi et al. |
| 6,893,662 | B2 | 5/2005 | Dittmar et al. |
| 6,905,709 | B2 | 6/2005 | Oshlack et al. |
| 6,923,988 | B2 | 8/2005 | Patel et al. |
| 6,932,981 | B2 | 8/2005 | Sen et al. |
| 6,946,146 | B2 | 9/2005 | Mulye |
| 7,008,950 | B1 * | 3/2006 | Ohkawa et al. ............... 514/278 |
| 7,160,559 | B1 * | 1/2007 | McGee et al. ............... 424/501 |
| 7,413,750 | B2 * | 8/2008 | Kolter et al. ............... 424/469 |
| 2002/0031546 | A1 | 3/2002 | Parekh et al. |
| 2002/0107173 | A1 * | 8/2002 | Friedhoff et al. |
| 2003/0091643 | A1 * | 5/2003 | Friesen et al. ............... 424/486 |
| 2003/0092737 | A1 | 5/2003 | Pierre et al. |
| 2003/0108606 | A1 | 6/2003 | Norden et al. |
| 2003/0118649 | A1 | 6/2003 | Gao et al. |
| 2003/0124176 | A1 * | 7/2003 | Hsu et al. |
| 2003/0133982 | A1 | 7/2003 | Heimlich et al. |
| 2003/0144255 | A1 | 7/2003 | Bain et al. |
| 2003/0147950 | A1 | 8/2003 | Platteeuw et al. |
| 2003/0180362 | A1 | 9/2003 | Park et al. |
| 2003/0211154 | A1 | 11/2003 | Mukherji et al. |
| 2003/0215509 | A1 | 11/2003 | Rao et al. |
| 2004/0005358 | A1 | 1/2004 | Slugg et al. |
| 2004/0022853 | A1 | 2/2004 | Ashton et al. |
| 2004/0028735 | A1 | 2/2004 | Kositprapa |
| 2004/0052844 | A1 | 3/2004 | Hsiao et al. |
| 2004/0052846 | A1 | 3/2004 | Prater et al. |
| 2004/0062800 | A1 | 4/2004 | Burnside et al. |
| 2004/0062805 | A1 | 4/2004 | Vandecruys |
| 2004/0087658 | A1 | 5/2004 | Moebius |
| 2004/0156896 | A1 | 8/2004 | Dixit et al. |
| 2004/0162263 | A1 | 8/2004 | Sands et al. |
| 2004/0175426 | A1 | 9/2004 | Ashton |
| 2004/0175428 | A1 | 9/2004 | Appel et al. |
| 2004/0185096 | A1 | 9/2004 | Oshlack et al. |
| 2004/0185097 | A1 | 9/2004 | Kannan et al. |
| 2004/0208824 | A1 * | 10/2004 | Parmelee et al. |
| 2004/0208928 | A1 | 10/2004 | Liao et al. |
| 2004/0208930 | A1 | 10/2004 | Yoneda et al. |
| 2004/0208932 | A1 | 10/2004 | Thembalath et al. |
| 2004/0213849 | A1 | 10/2004 | Sowden et al. |
| 2004/0219213 | A1 | 11/2004 | Burnside et al. |
| 2004/0228915 | A1 | 11/2004 | Noack et al. |
| 2004/0228916 | A1 | 11/2004 | Tanno et al. |
| 2004/0228917 | A1 | 11/2004 | Oshlack et al. |
| 2004/0234602 | A1 | 11/2004 | Fischer et al. |
| 2004/0241236 | A1 | 12/2004 | Li et al. |
| 2004/0247672 | A1 | 12/2004 | Tracy et al. |
| 2004/0253314 | A1 | 12/2004 | Petereit et al. |
| 2004/0254251 | A1 | 12/2004 | Firestone et al. |
| 2004/0258752 | A1 | 12/2004 | Paruthi et al. |
| 2004/0265375 | A1 | 12/2004 | Platteeuw et al. |
| 2005/0013863 | A1 | 1/2005 | Lim et al. |
| 2005/0019409 | A1 | 1/2005 | Edgren et al. |
| 2005/0025829 | A1 | 2/2005 | Kim |
| 2005/0042277 | A1 | 2/2005 | Srinivas et al. |
| 2005/0048116 | A1 | 3/2005 | Straub et al. |
| 2005/0048119 | A1 | 3/2005 | Nangia et al. |
| 2005/0053657 | A1 | 3/2005 | Rampal et al. |
| 2005/0058707 | A1 | 3/2005 | Reyes et al. |
| 2005/0064032 | A1 | 3/2005 | Lowe et al. |
| 2005/0064034 | A1 | 3/2005 | Li et al. |
| 2005/0074490 | A1 | 4/2005 | Lin et al. |
| 2005/0084531 | A1 | 4/2005 | Desai et al. |
| 2005/0089569 | A1 | 4/2005 | Bar-Shalom |
| 2005/0089570 | A1 | 4/2005 | Cruz et al. |
| 2005/0106245 | A1 | 5/2005 | Yuso |
| 2005/0107613 | A1 | 5/2005 | Tarur et al. |
| 2005/0112201 | A1 | 5/2005 | Baichwal et al. |
| 2005/0118266 | A1 | 6/2005 | Khan et al. |
| 2005/0118268 | A1 | 6/2005 | Percel et al. |
| 2005/0129751 | A1 | 6/2005 | Rothenberg et al. |
| 2005/0129759 | A1 | 6/2005 | Sojka |
| 2005/0129762 | A1 | 6/2005 | Heaton et al. |
| 2005/0136108 | A1 | 6/2005 | Yam et al. |
| 2005/0142088 | A1 | 6/2005 | Mizuno et al. |
| 2005/0142190 | A1 | 6/2005 | Adin et al. |
| 2005/0142199 | A1 | 6/2005 | Tian et al. |
| 2005/0152976 | A1 | 7/2005 | Chenevier et al. |
| 2005/0158380 | A1 | 7/2005 | Chawla et al. |
| 2005/0163843 | A1 | 7/2005 | Boehm et al. |
| 2005/0163844 | A1 | 7/2005 | Ashton |
| 2005/0163845 | A1 | 7/2005 | Conte et al. |
| 2005/0163846 | A1 | 7/2005 | Aoki |
| 2005/0169990 | A1 | 8/2005 | Kao et al. |
| 2005/0169992 | A1 | 8/2005 | Jao et al. |
| 2005/0169996 | A1 | 8/2005 | Dittmar et al. |
| 2005/0175696 | A1 | 8/2005 | Edgren et al. |
| 2005/0175700 | A1 | 8/2005 | Li et al. |
| 2005/0181044 | A1 | 8/2005 | Romero |
| 2005/0181047 | A1 | 8/2005 | Romero |
| 2005/0181048 | A1 | 8/2005 | Romero |
| 2005/0181053 | A1 | 8/2005 | Dittmar et al. |
| 2005/0186275 | A1 | 8/2005 | Ching-fen et al. |
| 2005/0191359 | A1 | 9/2005 | Goldshtein et al. |
| 2005/0202088 | A1 | 9/2005 | Hanshermann et al. |
| 2005/0208133 | A1 | 9/2005 | Tsutsumi et al. |
| 2005/0214368 | A1 | 9/2005 | Kawakami et al. |
| 2005/0214373 | A1 | 9/2005 | Desai et al. |
| 2005/0220875 | A1 | 10/2005 | Yang et al. |
| 2005/0220876 | A1 | 10/2005 | Hilfinger et al. |
| 2005/0220877 | A1 | 10/2005 | Patel et al. |
| 2005/0226929 | A1 | 10/2005 | Xie et al. |
| 2005/0232990 | A1 | 10/2005 | Boehm et al. |
| 2006/0142398 | A1 | 6/2006 | Went et al. |
| 2006/0177509 | A1 * | 8/2006 | Nagahara et al. ............... 424/470 |
| 2006/0210633 | A1 | 9/2006 | Dharmadhikari et al. |
| 2006/0246003 | A1 | 11/2006 | Kimura et al. |
| 2006/0251717 | A1 | 11/2006 | Firestone et al. |
| 2006/0252788 | A1 | 11/2006 | Went et al. |
| 2006/0280789 | A1 | 12/2006 | Ueki et al. |
| 2009/0191266 | A1 | 7/2009 | Vandecruys |

FOREIGN PATENT DOCUMENTS

| | | |
|---|---|---|
| CN | 1709229 A | 12/2005 |
| EP | 0138792 A2 | 4/1985 |

| | | | |
|---|---|---|---|
| EP | 0194838 A2 | 9/1986 |
| EP | 0 231 026 | 8/1987 |
| EP | 0 231 026 A1 | 8/1987 |
| EP | 0 297 866 | 1/1989 |
| EP | 0 368 947 | 5/1990 |
| EP | 0386967 A2 | 9/1990 |
| EP | 0 587 065 | 3/1994 |
| EP | 1027886 | 8/2000 |
| EP | 1027887 | 8/2000 |
| EP | 1086706 | 3/2001 |
| EP | 1318792 A2 | 6/2003 |
| EP | 1398040 A1 | 3/2004 |
| EP | 1454634 A1 | 9/2004 |
| EP | 1728512 A1 | 12/2006 |
| EP | 1832298 A1 | 9/2007 |
| EP | 1878444 A1 | 1/2008 |
| JP | 56-154420 A | 11/1981 |
| JP | 61-148115 | 7/1986 |
| JP | 03-193733 | 8/1991 |
| JP | 6-199657 | 7/1994 |
| JP | 08-133975 | 5/1996 |
| JP | 09-20663 | 1/1997 |
| JP | 09-188617 | 7/1997 |
| JP | 10-017497 | 1/1998 |
| JP | 2000-229888 | 8/2000 |
| JP | 2002-541090 | 12/2002 |
| JP | 2003-267889 | 9/2003 |
| NZ | 329839 A | 5/2000 |
| NZ | 504420 A | 8/2003 |
| NZ | 515023 A | 1/2004 |
| WO | WO-95/00501 A2 | 1/1995 |
| WO | WO-9714415 A1 | 4/1997 |
| WO | WO-9850077 A1 | 11/1998 |
| WO | WO-9933448 A1 | 7/1999 |
| WO | WO-00/19985 | 4/2000 |
| WO | WO 0018378 A1 | 4/2000 |
| WO | WO-00/30446 | 6/2000 |
| WO | WO-00/38686 | 7/2000 |
| WO | WO 01/22944 A1 * | 4/2001 |
| WO | WO-02/058676 | 8/2002 |
| WO | WO-03/000263 | 1/2003 |
| WO | WO-03/039530 | 5/2003 |
| WO | WO-03/101458 | 12/2003 |
| WO | WO04000317 A1 | 12/2003 |
| WO | WO 2004/017938 A2 | 3/2004 |
| WO | WO-2004/037234 A2 | 5/2004 |
| WO | WO-2004/037237 A1 | 5/2004 |
| WO | WO 2004/050058 | 6/2004 |
| WO | WO-2004/062577 A2 | 7/2004 |
| WO | WO 2004082665 A1 * | 9/2004 |
| WO | WO 2004087116 A2 | 10/2004 |
| WO | WO-2004/112768 A1 | 12/2004 |
| WO | WO 2005/065645 | 7/2005 |
| WO | WO-2005/065645 A1 | 7/2005 |
| WO | WO 2005/065661 | 7/2005 |
| WO | WO 2005092336 A1 | 10/2005 |
| WO | WO 2006/063025 | 6/2006 |
| WO | WO 2006/070930 | 7/2006 |
| WO | WO-2006/121560 A1 | 11/2006 |

OTHER PUBLICATIONS

Evonik Röhm GmbH, "Pharmacopoeial Monographs and Drug Master Files," Data Sheet for Registration, pp. 1-3 (2009).*
New Zealand Examination Report dated Sep. 7, 2009, for NZ Patent Application No. 562120.
Singapore Office Action issued in Application No. 200704810-1 dated May 5, 2009.
Database on Embase (STN), AN 1998276321, Nagarsenker, M.S. et al., "Solid dispersion for extended release of verapamil HCL.," Pharmacy and Pharmacology Communications, 1998, vol. 4, No. 7, pp. 331-334.
Database on Embase (STN), AN 2001021612, Rafiee-Tehrani, M. et al., "Effects of different polymers on the release characterstics of carbamazepine from stable controlled-release tablets prepared by the air suspension and wet granulation techniques," Acta Pharmaceutica, 2000, vol. 50, No. 4, pp. 291-301.
The Merck Index, Thirteenth Edition, 2001, p. 602, 3453. Donepeil., Merck & Co., Inc.
The Merck Index, Thirteenth Edition, 2001, p. 1480, 8323. Rivastigmine., Merck & Co., Inc.
Russian Drug Register (RDR) Encyclopedia of Drugs, 10th number, Chief Editor G.L. Vyshcovsky, M.; RDR-2003, pp. 726-727 (The Description of Rivastigmine) with its English Translation Cite No. BL WO 1998/50077.
STN search results establinshing equivalency of Eudragit L30D-55 and Eudragit L100-55; obtained Jan. 21, 2010.
U.S. Office Action dated Jan. 28, 2010, issued in co-pending U.S. Appl. No. 11/475,255.
English Translation International Preliminary Report on Patentablility Chapter I dated Jul. 3, 2007 issued in PCT/JP2005/023853.
English translation of International Preliminary Report on Patentability Chapter I dated Sep. 9, 2008 issued in PCT/JP2006/309021.
English Translation of the Written Opinion of the International Search Authority issued in PCT/JP2006/309021.
English Translation of the Written Opinion of the International Search Authority issued in PCT/JP2005/023853.
Extended European Search Report dated Jul. 6, 2010 issued in PCT/JP2006/309021.
International Search Report dated Feb. 21, 2006 issued in PCT/JP2005/024254.
International Preliminary Report on Patentability Chapter I dated Jul. 3, 2007 issued in PCT/JP2005/024254.
International Search Report dated Apr. 25, 2006 issued in PCT/JP2005/023853.
International Search Report dated Jul. 25, 2006, issued in PCT/JP2006/309021.
U.S. Office Action dated Jun. 29, 2010, issued in co-pending U.S. Appl. No. 11/793,722.
Rafiee-Tehrani, M. et al., "Effects of different polymers on the release characteristics of carbamazepine from stable controlled-release tablets prepared by the air suspension and wet granulation techniques," Acta Pharmaceutica, 2000, vol. 50, No. 4, pp. 291-301.
Voisin T. et al., "What are the Treatment Options for Patients with Severe Alzheimer's Disease," CNS Drugs, 2004, vol. 18(9), pp. 575-583.
Wenk, G.L. et al., "No Interaction Memantine With Acetylcholinesterase Inhibitors Approved for Clinical Use", Life Sciences, vol. 66, No. 12, pp. 1079-1083 (2000).
Written Opinion of the International Search Authority dated Feb. 14, 2006 issued in PCT/JP2005/024254.
Extended European Search Report dated Jul. 6, 2010 issued in European patent application No. 06745880.2.
Aulton, Pharmaceutics the science of dosage form design, Churchill Livingstone, 294, (2002).
Russian Office Action dated Aug. 13, 2010, from Application No. 2007139712/15(043487) filed Apr. 28, 2006.
Rafiee-Tehrani, M et al. Effects of different Polymers on the Release Characteristics of Carbamazepine from stable controlled-release tablets prepared by the air suspension and wet granulation techniques, Acta Pharmaceutica, 2000, vol. 50, No. 4, pp. 291-301 (Abstract Only).
Mexican Office Action dated Oct. 4, 2010 citing Reference No. BA (AU-2006241771-A1).
Indian Office Action of Application No. 4715/DELNP/2007, dated Oct. 27, 2010.
Aarsland, D, et al., (2002) J. Neurol. Neurosurg. Psych. 72; 99. 708-712.
Journal of Neurol. Neurosug Psychiatry 2002; 73: 351-354 (Correction to CA).
Office Action Issued Nov. 2, 2010 in U.S. Appl. No. 11/794,212.
Office Action of European Patent Application No. 06 745 880.2-2404 dated Dec. 16, 2010.
Office Action of Israel Patent Application No. 183650 dated Dec. 27, 2010.
U.S. Department of Health and Human Services Food and Drug Administration Center for Drug Evaluation and Research, "Guidance for Industry Dissolution Testing for Immediate Release Solid Oral Dosage Forms", Aug. 1997.
Russian Office Action dated Feb. 7, 2011, with an English translation for the Related Russian Pattent Application No. 2007139712.

U.S. Office Action dated Mar. 17, 2011, the U.S. Appl. No. 11/919,416.
New Zealand Office Action Issued in NZ Patent Application No. 562120 dated Jan. 18, 2010.
Ueki et al., Office Action dated Jul. 12, 2011 (U.S. Appl. No. 11/794,212).
Pollock, D. K., et al., Pharmaceutical Online (August 17, 1999).
Japanese Office Action (and English translation) mailed Jan. 24, 2012, in corresponding Japanese Application No. 2007-529288.
Egyptian Office Action (and English translation) mailed Jan. 15, 2012, in corresponding Egyptian Application No. PCT/NA 2007/000665.
Response (and English Translation) filed on Dec. 28, 2011, to the Japanese Office Action dated Nov. 11, 2011, in related Japanese Application No. 2007-529288.
Species Election mailed on Mar. 29, 2012, in corresponding U.S. Appl. No. 12/712,959.
Notice of Reasons for Rejection, with English Translation, issued in Japanese Patent Application No. 2007-529288, dated Nov. 11, 2011.
Japanese Office Action mailed Dec. 12, 2011 in corresponding Japanese Application 2006-550780 with English language translation.
Response filed on Jun. 27, 2012, to the Office Action issued on Mar. 27, 2012, in corresponding Egyptian Patent Application No. PCT 677/2007.
Response filed on Jul. 25, 2012, to the Office Action issued on Jun. 25, 2012, in corresponding Japanese Patent Application No. 2007-514845.
Response filed on Jul. 10, 2012, to the Office Action issued on Apr. 24, 2012, in corresponding Israeli patent application No. 183650.
Request for Reexamination filed on Jul. 31, 2012, to the Rejection Decision issued on Apr. 18, 2012, in corresponding Chinese Patent Application No. 200680014194.4.
Office Action issued on Jul. 4, 2012, in corresponding Philippines Patent Application No. 1-2007-502099.
Response filed on Sep. 3, 2012, in corresponding Philippines Patent Application No. 1-2007-502099.
Office Action mailed on Jul. 11, 2012, in U.S. Appl. No. 12/712,959.
Extended European Search Report issued on Sep. 6, 2012, in corresponding European Patent Application No. 05824466.6.
Response filed on Sep. 2, 2012, to the Office Action issued on Jul. 22, 2012, in corresponding Israeli Patent Application No. 183871.
Response filed on Sep. 5, 2012 to the Final Office Action issued on Jun. 14, 2012, in U.S. Appl. No. 12/910,313.
Advisory Action mailed on Sep. 19, 2012 in in U.S. Appl. No. 12/910,313.
Office Action mailed on Mar. 28, 2012, in U.S. Appl. No. 12/910,313.
Office Action issued on May 14, 2012, in Canadian Patent Application No. 2,604,617.
Response filed on Jun. 7, 2012, to the Office Action mailed on Mar. 28, 2012, in U.S. Appl. No. 12/910,313.
Final Office Action mailed on Jun. 14, 2012, in U.S. Appl. No. 12/910,313.
Extended European Search Report issued on Nov. 13, 2012 in corresponding European Patent Application No. 05822550.9.
Response filed on Oct. 15, 2012 to the Advisory Action issued on Sep. 19, 2012, U.S. Appl. No. 12/910,313.
Notice of Panel Decision from Pre-Appeal Brief Review mailed on Nov. 2, 2012 in U.S. Appl. No. 12/910,313.
Office Action issued on Oct. 15, 2012 in corresponding Israeli Patent Application No. 186179.
L. Ding et al., *Donepezil hydrochloride in the form of an enterically coated tablet, useful for the treatment of senile dementia*, Database WPI Section CH, Week 200561 Thomson Scientific, XP002686009, Abstract of CN 1608623, Apr. 27, 2005.
N. Fuwa et al., *Sustained-release fine particle prepn. contg. ibudilast—has the ibudilast heated with high mol. cpd. and oil/fat base then granulated*, Database WPI Section Ch. Week 199713 Thomson Scientific XP002686007, Abstract of JP 1995 0171870, Jan. 21, 1997.
Y. Yan et al., *Orally disintegrating tablet of memantine hydrochloride, and its preparation method and use*, Chemical Abstracts Service XP002686008, STN Accession No. 2006:1073087, Abstract of CN 1709229, Jun. 10, 2005.

Response filed on Jan. 13, 2013, to the Office Action issued on Oct. 15, 2012, in corresponding Israeli Patent Application No. 186179.
Office Action issued on Dec. 17, 2012, and response thereto filed on Jan. 16, 2013, in corresponding Philippine Patent Application No. 12007501200.
Office Action issued on Feb. 25, 2013, in corresponding Canadian Patent Application No. 2,604,617.
Office Action issued on Mar. 8, 2013, in corresponding Philippine Patent Application No. 12007501175.
Final Office Action issued on Jan. 31, 2013, in corresponding U.S. Appl. No. 12/712,959.
Response filed on Sep. 25, 2012, to the Office Action issued on May 14, 2012, in corresponding Canadian Patent Application No. 2604617.
Notice of Allowance on Sep. 27, 2012, in the corresponding Korean Patent Application No. 10-2007-7024881.
Response filed on Oct. 11, 2012, to the Office Action issued on Jul. 11, 2012, in U.S. Appl. No. 12/712,959.
Al-Rasheed et al., Saudi Pharmaceutical Journal, 6(1):99-101, 1998.
Bryson et al., Drugs & Aging, 10(3):234-239, 1997.
Brodaty et al., Degenerative and Neurological Disorders, S367, Abstract No. P.4.030.
Barner et al., Ann. Pharmacother., 32:70-77, 1998.
Controlled Release Technologies: Methods, Theory, and Applications, vol. II, Chapter 7, pp. 133-143.
Dimitrov, et al, "Study of Verapamil hydrochloride release from compressed hydrophilic Polyox-Wsr tablets"; International Journal of Pharmaceuticals 189, (1999); pp. 105/111.
Doody, Gerontology, 45(Suppl 1):23-32, 1999.
Eisai Co., Ltd. Information Meeting in Japan, 2 pages, Mar. 2, 2005.
Farlow, Clinical Therapeutics, 23(Suppl A):A13-A24, 2001.
Hogan et al., The Canadian Journal of Neurological Sciences, 29:306-314, 2002.
Hussar, American Druggist, pp. 48-55, Jan. 1998.
Hartmann, Susanne, et al., "Tolerability of memantine in combination with cholinesterase inhibitors in dementia therapy"; International Clinical Psychopharmacology, vol. 18, No. 2, pp. 81-85 (2003).
Jain, Kewal, K. "Evaluation of memantine for neuroprotecton in dementia"; Exp. Opin Invest Drugs 9 (6), pp. 1297-1406 (2000).
Jann et al., Clin Pharmacokinet, 41(10):719-739, 2002.
Jann, Am J Health-syst Pharm, 55(Suppl 2):S22-S25, 1998.
Kosasa et al., European Journal of Pharmacology, 380:101-107, 1999.
Krall et al., "The Annals of Pharmacotherapy", 33:441-450, 1999.
Khosla, R., et al, "Gastrointestinal transit of non-disintegrating tablets in fed subjects"; International Journal of Pharmaceutics, vol. 53, pp. 107-117, (1989).
Kohri, Naonori, et al, "Sustained Release of Nifedipine from Granules"; Journal of Pharmaceutical Sciences, vol. 1, pp. 57-61 (1986).
Matsui et al., Xenobiotica, 29(11):1059-1072, 1999.
MMW Fortschr. Med. (Suppl 2) p. 24, 26, 28-29, and cited literature thereof.
McGleenon et al., Br. J. Clin. Pharmacol., 48:471-480, 1999.
Maelicke, Clinical Therapeutics, 23(Suppl A):A8-A12, 2001.
Nokhodchi et al., European Journal of Pharmaceutics and Biopharmaceutics, 54:349-356, 2002.
Nordberg et al., Drug Safety, 19(6):465-480, 1998.
Nagy et al., Clinical Pharmacology & Therapeutics, Abstract No. PII-43, 2001.
Robinson, "Regulatory Guidelines for In-Vitro Versus In-Vitro Correlations of Controlled Release Oral Products", pp. 73-87.
Rogers et al., Br. J. Clin. Pharmacol., 46(Suppl 1):1-6, 1998.
Rogers, Dement Geriatr Cogn Disord, 9(Suppl 3):29-42, 1998.
Reyes et al., Degenerative and Neurological Disorders, S369-S370, Abstract No. P.4.036.
Reyes et al., Clinical Pharmacology & Therapeutics, Abstract No. PII-47, 2001.
Reyes et al., Clinical Pharmacology & Therapeutics, Abstract No. PII-46, 2001.
Ravic et al., Clinical Pharmacology & Therapeutics, Abstract No. PII-45, 2001.
Sugimoto et al., Current Medicinal Chemistry, 7:303-339, 2000.

Sugimoto et al., Jpn. J. Pharmacol., 89:7-20, 2002.

Streubel, A., et al, "pH-independent release of a weakly basic drug from water-insoluble and -soluble matrix tablets"; Journal of Controlled Release, 67, (2000), pp. 101-110.

Shigeta et al., CNS Drug Reviews, 7(4):353-368, 2001.

Sustained and Controlled Release of Drug Delivery Systems, Chapter 3, pp. 123-209.

Timmins, Peter, et al, "Optimization and Characterization of a pH-Independent Extended-Release Hydrophilic Matrix Tablet"; Pharmaceutical Development and Technology, 2(1), (1997), pp. 25-31.

Tatavarti, et al, "Influence of Methacrylic and Acrylic Acid Polymers on the Release Performance of Weakly Basic Drugs from Sustained Release Hydrophilic Matrices"; Journal of Pharmaceutical Sciences, vol. 93, No. 9, (Sep. 2004), pp. 2319-2331.

Takka, et al, "Effect of anionic polymers on the release of propranolol hydrochloride from matrix tablets"; European Journal of Pharmaceutical Sciences, vol. 52, (2001), pp. 75-82.

Tariot, Pierre N., M.D., et al., "Memantine Treatment in Patients With Moderate to Severe Alzheimer Disease Already Receiving Donepezil—A Randomized Controlled Trial"; JAMA, vol. 291, No. 3, pp. 317-324 (Jan. 21, 2004).

Tiseo et al., Br. J. Clin. Pharmacol., 46(Suppl 1):13-18, 1998.
Tiseo et al., Br. J. Clin. Pharmacol., 46(Suppl 1):51-55, 1998.
Tiseo et al., Br. J. Clin. Pharmacol., 46(Suppl 1):25-29, 1998.
Tiseo et al., Br. J. Clin. Pharmacol., 46(Suppl 1):56-60, 1998.
Whitehouse, Drugs of Today, 34(4):321-326, 1998.

Windisch, M., et al, "Current drug and future hopes in the treatment of Alzheimer's disease"; J. Neural Transm. Supt. 62, pp. 149-164 (2002).

Wenk, Gary L., et al, "No Interaction of Memantine With Acetylcholinesterase Inhibitors Approved for Clinical Use"; Life Science, vol. 18, No. 2, pp. 81-85 (2003).

Yamanishi et al., "Discovery and Development of Donepeziil Hydrochloride (Aricept), A New Drug for Alzheimer's Disease", Abstract No. S18-2.

Yamanishi et al., Japanese Journal of Pharmacology, 79(Suppl 1):259, 1999.

Yasui-Furukori et al., Journal of Chromatography B, 768:261-265, 2002.

Zhao et al., J. Clin. Pharmacol., 43:180-186, 2003.

Zhang Bai-Fang, et al. "Bis (7)-Tacrine, a Promising Anti-Alzheimer's Agent, Attenuates Glutamate-Induced Cell Injury in Primary Cultured Cerebrocortical Neurons of Rats"; Whuhan University Journal of Natural Sciences, vol. 6, No. 3, pp. 737-741 (2001).

International Search Report, International Application No. PCT/JP2005/023583, with English-language language translation.

Australian Office Action, dated Feb. 11, 2009 in corresponding AU Application No. 2005320609.

Office Action issued on Mar. 27, 2012, in Egyptian Patent Application No. PCT/NA2007/000677.

Eudragit, Technical Information: Eudragit RL 100, Fudragif RL PO, Eudragit RS 100, and Eudragit RS PO, pp. 1-7 (2011).

Office Action mailed on May 3, 2012, in U.S. Appl. No. 11/793,722.

Response filed on Apr. 19, 2012 to the Election Requirement issued on Mar. 29, 2012 in U.S. Appl. No. 12/712,959.

Response filed on Apr. 2, 2012, in reply to the Office Action dated Jan. 15, 2012 issued in the Egyptian Application No. PCT665/2007, with English translation of amended claims.

Office Action issued on Apr. 24, 2012 in the Israeli Application No. 183650 with English translation.

Appeal and Amendment filed on Apr. 24, 2012, in reply to the Final Rejection dated Jan. 24, 2012, issued in Japanese application No. 2007-529288, with English translations.

Verapamil HCl website: http://www.sigmaaldrich.com/catalog/product/sigma/v4629?1ang-en®ion=US; accessed online Mar. 21, 2012.

Propranolol HCl website: http:/www.chemicalbook.com/ChemicalProductProperty_EN_CB5112834.htm; accessed online Mar. 21, 2012.

P.G. Weiler et al., *Propranolol for the control of disruptive behavior in senile dementia*, 1(4) J. Geriatr. Psychiatry Neurol. 226-230 (abstract only).

Response filed on Mar. 20, 2013 in European patent application No. 05824466.6.

Response filed on Apr. 10, 2013 in European patent application No. 05822550.9.

Response filed Apr. 5, 2013, in U.S. Appl. No. 12/712,959.

Response filed on Sep. 2, 2012, in Israeli Patent Application No. 183871.

Response filed May 14, 2013, in U.S. Appl. No. 12/910,313.

Notification of Reexamination mailed on Apr. 27, 2013, in Chinese Patent Appl. No. CN200680014194.4.

Response filed on Apr. 29, 2013, in Philippine Patent Appl. No. 12007501175.

Response filed May 17, 2013, in U.S. Appl. No. 11/794,212.

* cited by examiner

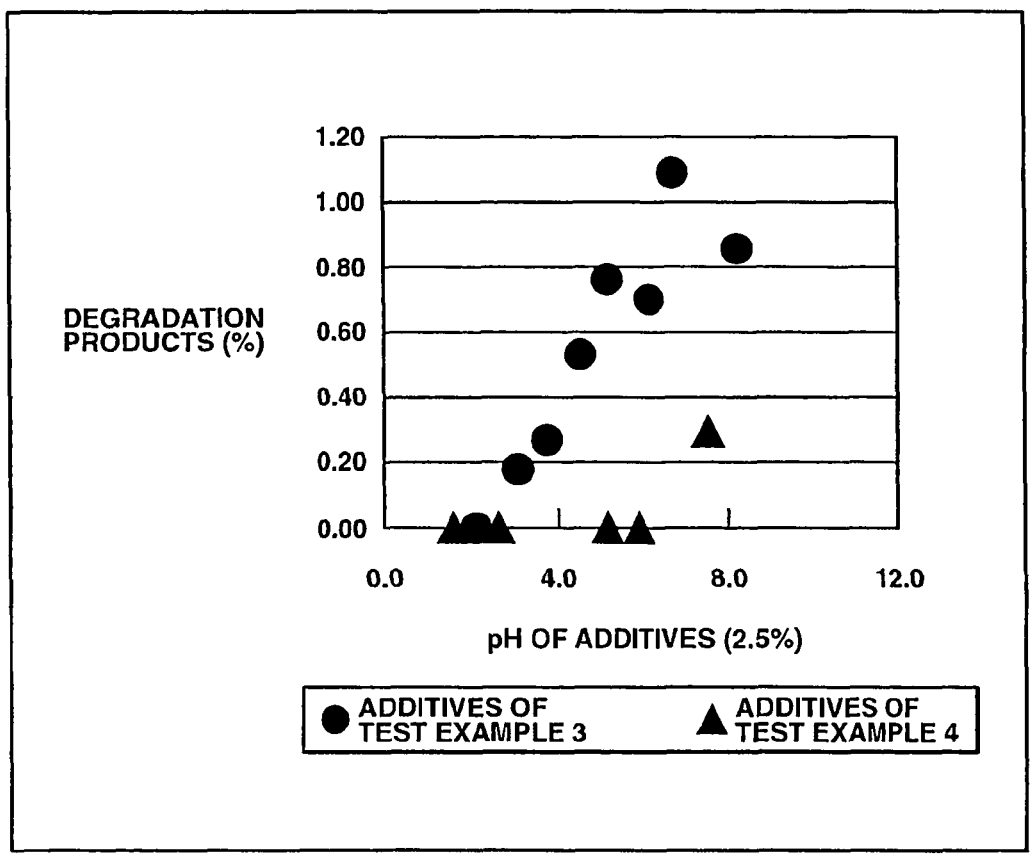

METHOD FOR STABILIZING ANTI-DEMENTIA DRUG

TECHNICAL FIELD

The present invention relates to stabilization of an anti-dementia drug in a composition containing the anti-dementia drug. More particularly, the present invention relates to the stabilization of the anti-dementia drug in a pharmaceutical composition which has the sustained-release characteristics, and which contains the anti-dementia drug having a tertiary amino group.

BACKGROUND ART

In recent years, care for dementia including a senile dementia, an Alzheimer-type dementia or the like has become a social problem, and many therapeutic drugs are being developed. Of these, donepezil, which is available as a hydrochloride in a tablet or a granule form, is seen as being highly useful as a therapeutic drug for mild and moderate Alzheimer's dementia because of its acetylcholinesterase inhibiting action. Recently, a tablet which disintegrates in the mouth have been marketed for patients who have trouble swallowing, and transdermal administration by an ointment preparation has been proposed for cases in which oral administration is difficult (For examples, see Patent Document 1: Japanese Patent Application Laid-Open No. H11-315016).

Such development of the pharmaceutical composition suitable for the conditions and symptoms of the patient is extremely important from the standpoint of compliance or quality of life. In this sense, a sustained-release preparation is useful for the anti-dementia drug because the sustained-release characteristics of the drug allows the number of drug administrations to be reduced while providing the same or better therapeutic effects, potentially improving compliance.

In general, the sustained-release preparation containing the drug which is physiologically active can be classified into two type preparations, (1) a matrix type preparation, in which the drug and a sustained-release base are distributed uniformly in the preparation, and (2) a sustained-release coated type preparation, in which release is controlled by coating a surface of a core particle or a core tablet containing a physiologically active drug with a sustained-release coating.

Matrix type sustained-release preparations have a matrix in which the drug and the sustained-release base are present uniformly. The matrix is generally used as is as a tablet or a granule, and may be given a light-shielding coating or the like. Sustained-release coated preparations include those in which a coating which comprises the sustained-release base is applied to a core of the granule, the tablet or the like containing a drug, or those in which a layer containing the drug is applied on a core particle consisting of crystalline cellulose or sucrose which are so-called nonpareil, followed by another sustained-release coating. The sustained-release characteristics are also controlled in some cases by means of multiple layers of coating containing the drug or coating containing the sustained-release base.

However, because these sustained-release preparations now comprise the sustained-release base and other additives which were not included in conventional, fast-dissolving tablet and the like, care must be taken that the stability of the drug is not affected. In particular, many anti-dementia drugs are basic drugs containing an amino group, and in general, a highly reactive functional group such as the amino group which is nucleophilic has a property of easily producing degradation products, when reacting with carbonyl carbon, peroxide, oxygen or the like.

Since the degradation products of the drug or additives can affect the stability or efficacy of the pharmaceutical products, means of preventing generation of such degradation products or severely inhibiting the produced amounts are being studied in the field of preparation development. Regarding a method for stabilizing the anti-dementia drug, a composition containing an organic acid has been disclosed for stabilizing donepezil against light (For examples, see Patent Document 2: Japanese Patent Application Laid-Open No. H11-106353). It was reported that the light-stabilizing effect was evaluated as the effect of adding an organic acid to donepezil in an aqueous ethanol solution, and a residual ratio of donepezil was higher in a solution to which tosylic acid, mesylic acid, citric acid or the like had been added than in a solution with no added organic acids.

DISCLOSURE OF INVENTION

Thus, there is demand for a pharmaceutical composition which improves compliance for the anti-dementia drug, such as a pharmaceutical composition having the sustained-release characteristics. On the other hand, as with the ordinary drugs, it is requested for the sustained-release preparation to ensure storage stability. In addition, because the anti-dementia drug is often administered for a prolonged period, even in the case of preparation which has a sustained-release function, there is demand for the pharmaceutical composition and a method for manufacturing the pharmaceutical composition, which can be manufactured easily and cheaply. Accordingly, it is an object of the present invention to provide a stabilization of the anti-dementia drug in the pharmaceutical composition containing the anti-dementia drug. More specifically, it is an object of the present invention to provide a pharmaceutical composition containing the anti-dementia, which has the sustained-release characteristics and which has excellent stability of the anti-dementia drug, and a method for manufacturing the pharmaceutical composition, and a method for stabilizing an anti-dementia drug in the pharmaceutical composition.

Under these circumstances, the present inventors carried out extensive studies on pharmaceutical compositions containing anti-dementia drugs. As a result, the present inventors have discovered that degradation products derived from donepezil hydrochloride are produced in the matrix type sustained-release preparation containing donepezil hydrochloride as the anti-dementia and ethylcellulose which is a high molecular weight basic substance as a sustained-release base, and a high molecular weight acidic substance effectively prevents or inhibits the degradation products which are produced when the anti-dementia drug comes into contact with the high molecular weight basic substance which is a sustained-release base, and the high molecular weight acidic substance has also combined effects with a low molecular weight acidic substance and an anti-oxidant, thereby arriving at the present invention.

Accordingly, the present invention relates the pharmaceutical composition containing the anti-dementia drug and the sustained-release base, with excellent storage stability of the anti-dementia drug, wherein the high molecular weight acidic substance is contained for stabilizing the anti-dementia drug. Moreover, a commercially available enteric polymer substance or the like can be used as the high molecular weight acidic substance, which can be easily mixed or granulated together with the anti-dementia drug and the sustained-release base to easily manufacture the pharmaceutical composition according to the present invention.

In the first aspect of the present invention, the present invention relates to a method for stabilizing an anti-dementia drug comprising adding a high molecular weight acidic substance in a pharmaceutical composition containing the anti-dementia drug and a high molecular weight basic substance. By adding a high molecular weight acidic substance it is possible to inhibit the degradation products of the anti-dementia drug, which are produced by contact of the anti-dementia drug with the high molecular weight basic substance. Moreover, according to a preferred aspect of the method according to the present invention, there is the method for stabilizing the anti-dementia drug wherein at least one of a low molecular weight acidic substance and an anti-oxidant is added in the pharmaceutical composition according to the present invention.

In the second aspect of the present invention, there is provided a pharmaceutical composition containing an anti-dementia drug and a high molecular weight basic substance, in which the composition comprises a high molecular weight acidic substance for stabilizing the anti-dementia drug. The pharmaceutical composition according to the present invention also comprises at least one of a low molecular weight acidic substance and an anti-oxidant. More particularly, the pharmaceutical composition is a composition such as a matrix type sustained-release preparation which comprises a matrix which is a mixture of an anti-dementia drug, a high molecular weight basic substance and a high molecular weight acidic substance for stabilizing the anti-dementia drug, or is a composition such as a sustained-release coated preparation which comprises a core containing the anti-dementia drug and a coating layer containing the high molecular weight basic substance coated on the above-mentioned core, wherein a high molecular weight acidic substance is mixed in at least one of the above-mentioned core and the above-mentioned coating layer.

In particular, the pharmaceutical composition according to the present invention is a pharmaceutical composition, comprising: (1) a basic drug or a salt thereof which has solubility of 1 mg/mL or more in the 0.1 N hydrochloric acid solution, and the 50 mM phosphate buffer, pH 6 and which has solubility of 0.2 mg/mL or less in the 50 mM phosphate buffer, pH 8, and the solubility of the basic drug or the salt thereof in the 50 mM phosphate buffer, pH 6.8 being at least twice its solubility in the 50 mM phosphate buffer, pH 8 and being not more than half its solubility in the 50 mM phosphate buffer, pH 6; (2) at least one enteric polymer substance (high molecular weight acidic substance) and (3) at least one water-insoluble polymer substance (high molecular weight basic substance).

In the third aspect of the present invention, there is provided a manufacturing method for effectively achieving the dementia drug stabilizing effects of the present invention, in other words, a method for manufacturing a pharmaceutical composition containing an anti-dementia drug and a high molecular weight basic substance, comprising mixing step and granulating step, wherein a high molecular weight acidic substance for stabilizing the anti-dementia drug is added to a mixture of the anti-dementia drug and the high molecular weight basic substance during at least one of the mixing step and the granulating step. According to a preferred aspect of the manufacturing method according to the present invention, at least one of a low molecular weight acidic substance and an anti-oxidant can be added in addition to the high molecular weight acidic substance to stabilize the anti-dementia drug. In a more preferred aspect; at least one of the high molecular weight acidic substance, the low molecular weight acidic substance and the anti-oxidant is added in the form of a solution or suspension during at least one of the mixing step and the granulating step. In a particularly preferred aspect of the manufacturing method according to the present invention, after adding the high molecular weight acidic substance as a powder in the mixing step, at least one of the low molecular weight acidic substance and the anti-oxidant can be added in the form of a solution or suspension to the mixture in the granulating step.

Further, in the third aspect of the present invention, there is provided a method for manufacturing a pharmaceutical composition, comprising the steps of: mixing (1) a basic drug or a salt thereof which has solubility in the 0.1 N hydrochloric acid solution, and the 50 mM phosphate buffer, pH 6 being 1 mg/mL or more, solubility in the 50 mM phosphate buffer, pH 8 being 0.2 mg/mL or less, and which has solubility in the 50 mM phosphate buffer, pH 6.8 being at least twice its solubility in the 50 mM phosphate buffer, pH 8 and being not more than half its solubility in the 50 mM phosphate buffer, pH 6, with (2) at least one enteric polymer (high molecular weight acidic substance) and (3) at least one water-insoluble polymer substance (high molecular weight basic substance); and compression-molding the mixture obtained in the mixing step.

Furthermore, in the fourth mode of the present invention, there is provided a use of a high molecular weight acidic substance for controlling an anti-dementia drug degradation products produced by contact between the anti-dementia drug and the high molecular weight basic substance. This is a new use which has been discovered for the high molecular weight acidic substances. In this case, degradation products can be effectively inhibited through a concomitant use of a low molecular weight acidic substance and an anti-oxidant.

According to a preferred aspect of the present invention, the anti-dementia drug is a compound having a tertiary amino group. According to a more preferred aspect of the present invention, the anti-dementia drug is selected from the group consisting of rivastigmine, galantamine, donepezil, 3-[1-(phenylmethyl)piperidin-4-yl]-1-(2,3,4,5-tetrahydro-1H-1-benzazepin-8-yl)-1-propane and 5,7-dihydro-3-[2-[1-(phenylmethyl)-4-peperidinyl]ethyl]6H-pyrrolo[4,5-f]-1,2-benzisoxazol-6-one and pharmaceutically acceptable salts thereof. In a particularly preferred aspect, the anti-dementia drug is donepezil or a pharmaceutically acceptable salt thereof.

Moreover, according to a preferred aspect of the present invention, the high molecular weight basic substance is at least one selected from the group consisting of ethylcellulose, ethyl acrylate-methyl methacrylate copolymer and polyethylene oxide. In a more preferred aspect, the high molecular weight basic substance is either ethylcellulose or ethyl acrylate-methyl methacrylate copolymer, and in a particularly preferred aspect, the high molecular weight basic substance is ethylcellulose. The high molecular weight basic substance may also be any of water-insoluble polymer substances.

Further, according to a preferred aspect of the present invention, the high molecular weight acidic substance is an enteric polymer substance. In a more preferred aspect, the high molecular weight acidic substance is at least one selected from the group consisting of methacrylic acid-ethyl acrylate copolymer, methacrylic acid-methyl methacrylate copolymer, hydroxypropyl methylcellulose phthalate and hydroxypropyl methylcellulose acetate succinate. In a particularly preferred aspect, the high molecular weight acidic substance is methacrylic acid-ethyl acrylate copolymer. In a preferred aspect of an amount of the high molecular weight acidic substance, the amount is generally 0.1 to 90 parts by weight, preferably 1 to 70 parts by weight, more preferably 5 to 60 parts by weight, still more preferably 10 to 50 parts by weight, based on 100 parts by weight of the pharmaceutical composition according to the present invention.

Furthermore, according to a preferred aspect of the present invention, the low molecular weight acidic substance is at least one selected from the group consisting of carboxylic acids, sulfonic acids, hydroxy acids, acidic amino acids and inorganic acids. In a more preferred aspect, the low molecular weight acidic substance is at least one selected from the group consisting of hydroxy acids, acidic amino acids and inorganic acids. In a particularly preferred aspect, the low molecular weight acidic substance is at least one selected from the group consisting of hydroxy acids and acidic amino acids.

More specifically, the low molecular weight acidic substance is at least one selected from the group consisting of succinic acid, tartaric acid, citric acid, fumaric acid, maleic acid, malic acid, aspartic acid, glutamic acid, glutamic acid hydrochloride, hydrochloric acid and phosphoric acid. In a more preferred aspect, the low molecular weight acidic substance is at least one selected from the group consisting of succinic acid, tartaric acid, citric acid, malic acid, aspartic acid, glutamic acid, glutamic acid hydrochloride, hydrochloric acid and phosphoric acid. In a particularly preferred aspect, the low molecular weight acidic substance is at least one selected from the group consisting of citric acid, aspartic acid and hydrochloric acid. An amount of the low molecular weight acidic substance is generally 0.05 to 4 parts by weight, preferably 0.1 to 3 parts by weight, more preferably 0.15 to 2 parts by weight, still more preferably 0.15 to 1.5 parts by weight, based on 100 parts by weight of the pharmaceutical composition according to the present invention.

According to a preferred aspect of the present invention, the anti-oxidant is at least one of the ascorbic acids and sulfur-containing amino acids. In a more preferred aspect, the anti-oxidant is at least one selected from the group consisting of methionine, ascorbic acid and cysteine hydrochloride. An amount of the anti-oxidant is generally 0.01 to 10 parts by weight, preferably 0.02 to 5 parts by weight, more preferably 0.05 to 2 parts by weight, based on 1 part by weight of the drug. Although the amount of the anti-oxidant is not particularly limited, but for example, the amount of the anti-oxidant is generally 0.001 to 5 parts by weight, preferably 0.01 to 3 parts by weight, more preferably 0.1 to 2 parts by weight, still more preferably 0.15 to 1.5 parts by weight, based on 100 parts by weight of the pharmaceutical composition according to the present invention.

The pharmaceutical composition according to the first through third aspects of the present invention is preferably a sustained-release preparation, and more preferably a matrix type sustained-release preparation. Moreover, examples of dosage form of the pharmaceutical composition include preferably tablets, capsules, granules or fine granules. Accordingly, the pharmaceutical composition according to a particularly preferred aspect of the present invention is a matrix type sustained-release preparation containing donepezil or a pharmaceutically acceptable salt thereof, the high molecular weight basic substance and the high molecular weight acidic substance, or a matrix type sustained-release preparation containing donepezil or a pharmaceutically acceptable salt thereof, the high molecular weight basic substance, the high molecular weight acidic substance and at least one of the low molecular weight acidic substance and the anti-oxidant.

ADVANTAGEOUS EFFECTS OF THE INVENTION

According to the present invention, in the pharmaceutical composition containing an anti-dementia drug and a sustained-release base, a method is provided for preventing or inhibiting degradation products due to the contact of the anti-dementia drug with the sustained-release base, namely the present invention can provide a method for stabilizing the anti-dementia drug in the pharmaceutical composition. Moreover, because the pharmaceutical composition according to the present invention is of high quality and highly suitable for compliance, the present invention provide pharmaceutical products, particularly anti-dementia drugs, which can be taken without worry and with less burden on patients and their caregivers. The present invention also provides a simple method for manufacturing the pharmaceutical composition in which sustained-release characteristics are controlled and the anti-dementia drug is stabilized without the use of specialized coating techniques or manufacturing equipment.

BRIEF DESCRIPTION OF DRAWINGS

FIG. 1 shows the relationship between pH of 2.5% aqueous solutions or suspensions of various additives and amounts of degradation products after granules containing various additives in open (unsealed) container were stored for 2 weeks at 60° C., 75% RH.

BEST MODE FOR CARRYING OUT THE INVENTION

Embodiments of the present invention will be explained in the following. The following embodiments are examples for explaining the present invention, and it is not intended that the present invention be limited only to these embodiments. The present invention can be implemented in various modes without departing from the spirit and the scope of the invention.

(Anti-dementia Drug)

There are no particular limitations on the anti-dementia drug used in the present invention as long as the anti-dementia drug is a basic drug having a primary, secondary or tertiary amino group, but preferably the anti-dementia drug has the tertiary amino group. Examples of the anti-dementia drug having the primary amino group include tacrine, memantine and pharmaceutically acceptable salts thereof. Examples of the anti-dementia drug having the tertiary amino group include rivastigmine, galantamine, donepezil, 3-[1-(phenylmethyl)piperidin-4-yl]-1-(2,3,4,5-tetrahydro-1H-1-benzazepin-8-yl)-1-propane and 5,7-dihydro-3-[2-[1-(phenylmethyl)-4-piperidinyl]ethyl]-6H-pyrrolo[4,5-f]-1,2-benzisoxazol-6-one and pharmaceutically acceptable salts thereof. Preferable examples of the anti-dementia drug having the primary amino group are tacrine and memantine hydrochloride. Preferable examples of the anti-dementia drug having the tertiary amino group are rivastigmine tartrate, galantamine hydrobromide, donepezil hydrochloride (chemical name (±)-2-[(1-benzylpiperidin-4-yl)methyl]-5,6-dimethoxyindan-1-one monohydrochloride), 3-[1-(phenylmethyl)piperidin-4-yl]-1-(2,3,4,5-tetrahydro-1H-1-benzazepin-8-yl)-1-propane fumarate (TAK-147) and 5,7-dihydro-3-[2-[1-(phenylmethyl)-4-piperidinyl]ethyl]-6H-pyrrolo[4,5-f]-1,2-benzisoxazol-6-one maleate (CP118954). More preferably, the anti-dementia drug is donepezil hydrochloride, TAK-147 or CP118954, and most preferably the anti-dementia drug is donepezil hydrochloride. Note that the anti-dementia drug may be used either in free form or as an organic or inorganic salt, with an organic or inorganic salt being preferred and an inorganic salt being particularly preferred. More specifically, examples of the salts include, but are not limited to, hydrochlorides, sulfates, acetates, phosphates, carbonates, mesylates, tartrates, citrates, tosylates or the like.

There are no particular limitations on the solubility of the basic drug or the salt thereof used in the present invention with respect to acidic aqueous solutions, neutral aqueous solutions or basic aqueous solutions, but the solubility of the basic drug or the salt thereof in the acidic aqueous solution and the neutral aqueous solution is higher than its solubility in the basic aqueous solution. Herein, for use in preparation of these aqueous solutions, examples for this use includes, but are not limited to, a phosphate buffer (for instance, buffers prepared with 50 mM sodium phosphate solution and hydrochloric acid), buffers such as G. L. Miller's buffer, Atkins-Pantin's buffer, Good's buffer or the like, 0.1 N hydrochloric acid, 0.1 mol/L sodium hydroxide solution or the like. Note that the solubility used in the present invention refers to solubility wherein a solution temperature is 25° C.

The term "solubility in an acidic aqueous solution" used in the present invention means that a solubility of the basic drug or the salt thereof in a solution exhibiting an acidic property when dissolving the basic drug or the salt thereof in a buffer or the like. Similarly, the term "solubility in a neutral (basic) aqueous solution used in the present invention means that a solubility of the basic drug or the salt thereof in a solution exhibiting a neutral (basic) property when dissolving the basic drug or the salt thereof in a buffer or the like.

By way of example, the basic drug or the salt thereof used in the present invention has a higher solubility in the acidic aqueous solution, pH 3.0 and the neutral aqueous solution, pH 6.0 than in the basic aqueous solution, pH 8.0. The term "solubility in the acidic aqueous solution, pH 3.0" used herein means that a solubility of the basic drug or the salt thereof in the acidic solution having a pH 3.0 when dissolving the basic drug or the salt thereof in a buffer or the like. The term "solubility in the neutral aqueous solution, pH 6.0" used herein means that a solubility of the basic drug or the salt thereof in a solution having a pH 6.0 when dissolving the basic drug or the salt thereof in a buffer or the like. Similarly, the term "solubility in the basic aqueous solution, pH 8.0" used herein means that a solubility of the basic drug or the salt thereof in a solution having a pH 8.0 when dissolving the basic drug or the salt thereof in a buffer or the like.

By way of another example, the basic drug or the salt thereof used in the present invention has a higher solubility in a 0.1 N hydrochloric acid solution and the neutral aqueous solution, pH 6.0 than in the basic aqueous solution, pH 8.0. The term "solubility in the 0.1 N hydrochloric acid solution" used herein means that a solubility of the basic drug or the salt thereof when dissolving the basic drug or the salt thereof in the 0.1 N hydrochloric acid solution. For example, the solution of donepezil hydrochloride dissolved in the 0.1 N hydrochloric acid solution shows a pH range of from about 1 to about 2.

Preferably, the basic drug or the salt thereof used in the present invention has a solubility in the 0.1 N hydrochloric acid solution and the neutral aqueous solution, pH 6.0 being higher than in the basic aqueous solution, pH 8.0 and a solubility in the neutral aqueous solution, pH 6.8 being at least twice its solubility in the basic aqueous solution, pH 8.0, and being not more than half its solubility in the neutral aqueous solution, pH 6.0. The term "solubility in the neutral aqueous solution, pH 6.8" used herein means that a solubility of the basic drug or the salt thereof in a solution having a pH 6.8 when dissolving the basic drug or the salt thereof in a buffer or the like.

More specifically, there are no particular limitations as long as the solubility of the basic drug or the salt thereof in the 0.1 N hydrochloric acid solution and the neutral aqueous solution, pH 6.0 is 1 mg/mL or more, the solubility of the basic drug or the salt thereof in the basic aqueous solution, pH 8.0 is 0.2 mg/mL or less, and the solubility of the basic drug or the salt thereof in the neutral aqueous solution, pH 6.8 is two or more times its solubility in the basic aqueous solution, pH 8.0 and is not more than half its solubility in the neutral aqueous solution, pH 6.0. That is, the solubility of the basic drug or the salt thereof in the 0.1 N hydrochloric acid solution and the neutral aqueous solution, pH 6.0 is not particularly limited as long as the above solubility is 1 mg/mL or more. The above solubility is generally 1 to 1000 mg/mL, preferably 5 to 200 mg/mL, more preferably 5 to 100 mg/mL, still more preferably 10 to 80 mg/mL. The solubility of the basic drug or the salt thereof in the basic aqueous solution, pH 8.0 is not particularly limited as long as the above solubility is 0.2 mg/mL or less. The above solubility is generally 0.0001 to 0.2 mg/mL, preferably 0.0005 to 0.1 mg/mL, more preferably 0.001 to 0.05 mg/mL, still more preferably 0.002 to 0.03 mg/mL. Moreover, the solubility of the basic drug or the salt thereof in the neutral aqueous solution, pH 6.8 is not particularly limited as long as the above solubility is at least twice its solubility in the basic aqueous solution, pH 8.0 and is not more than ½ solubility in the neutral aqueous solution, pH 6.0. The above solubility is preferably at least 3 times solubility in the basic aqueous solution, pH 8.0 and is not more than ⅓ solubility in the neutral aqueous solution, pH 6.0, more preferably at least 5 times solubility in the basic aqueous solution, pH 8.0 and not more than ⅕ solubility in the neutral aqueous solution, pH 6.0, still more preferably at least 10 times solubility in the basic aqueous solution, pH 8.0 and not more than 1/10 solubility in the neutral aqueous solution, pH 6.0.

By way of still another example, the solubility of the basic drug or the salt thereof used in the present invention in the 0.1 N hydrochloric acid solution and the 50 mM phosphate buffer, pH 6.0 is higher than its solubility in the 50 mM phosphate buffer, pH 8.0. The term "solubility in the 50 mM phosphate buffer, pH 6.0" used herein means a solubility of the basic drug or the salt thereof in the 50 mM phosphate buffer having pH 6.0 when dissolving the basic drug or the salt thereof in the 50 mM phosphate buffer. Similarly, the term "solubility in the 50 mM phosphate buffer, pH 8.0" used herein means a solubility of the basic drug or the salt thereof in the 50 mM phosphate buffer having pH 8.0 when dissolving the basic drug or the salt thereof in the 50 mM phosphate buffer.

Preferably, the solubility of the basic drug or the salt thereof in the 0.1 N hydrochloric acid solution and the 50 mM phosphate buffer, pH 6.0 is higher than its solubility in the 50 mM phosphate buffer, pH 8.0, and the solubility in the 50 mM phosphate buffer, pH 6.8 is two or more times its solubility in the 50 mM phosphate buffer, pH 8.0 and is not more than half its solubility in the 50 mM phosphate buffer, pH 6.0. To be more specific, there are no particular limitations as long as the solubility of the basic drug or the salt thereof in the 0.1 N hydrochloric acid solution and the 50 mM phosphate buffer, pH 6.0 is 1 mg/mL or more, the solubility of the basic drug or the salt thereof in the 50 mM phosphate buffer, pH 8.0 is 0.2 mg/mL or less, and the solubility of the basic drug or the salt thereof in the 50 mM phosphate buffer, pH 6.8 is two or more times its solubility in the 50 mM phosphate buffer, pH 8.0 and is not more than half its solubility in the 50 mM phosphate buffer, pH 6.0. That is, the solubility of the basic drug or the salt thereof in the 0.1 N hydrochloric acid solution and the 50 mM phosphate buffer, pH 6.0 is not particularly limited as long as the above solubility is 1 mg/mL or more. The above solubility is generally 1 to 1000 mg/mL, preferably 5 to 200 mg/mL, more preferably 5 to 100 mg/mL, still more preferably 10 to 80 mg/mL. The solubility of the basic drug or the salt thereof in the 50 mM phosphate buffer, pH 8.0 is not particularly limited as long as the above solubility is 0.2 mg/mL or less. The above solubility is generally 0.0001 to 0.2 mg/mL, preferably 0.0005 to 0.1 mg/mL, more preferably 0.001 to 0.05 mg/mL, still more preferably 0.002 to 0.03 mg/mL. Moreover, the solubility of the basic drug or the salt thereof in the 50 mM phosphate buffer, pH 6.8 is not particularly limited as long as the above solubility is at least twice its solubility in the 50 mM phosphate buffer, pH 8.0 and is not more than ½ solubility in the 50 mM phosphate buffer, pH 6.0. The above solubility is preferably at least 3 times solubility in the 50 mM phosphate buffer, pH 8.0 and is not more than ⅓ solubility in the 50 mM phosphate buffer, pH 6.0, more preferably at least 5 times solubility in the 50 mM phosphate buffer, pH 8.0 and not more than ⅕ solubility in the 50 mM phosphate buffer, pH 6.0, still more preferably at least 10 times solubility in the 50 mM phosphate buffer, pH 8.0 and not more than ¹⁄₁₀ solubility in the 50 mM phosphate buffer, pH 6.0.

For example, donepezil hydrochloride is characterized by its solubility of 11 to 16 mg/mL in an acidic aqueous solution, pH 3.0 and a neutral aqueous solution, pH 6.0 and 0.1 mg/mL or less in a basic aqueous solution, pH 8.0. Moreover, donepezil hydrochloride is a weakly basic drug or a salt thereof having one tertiary amino group, which has been widely used for Alzheimer's disease dementia, and is characterized by its solubility in the neutral aqueous solution, pH 6.8 being at least twice solubility in the basic aqueous solution, pH 8.0 and being not more than ½ solubility in the neutral aqueous solution, pH 6.0.

Alternatively, donepezil hydrochloride is a weakly basic drug or a salt thereof having one tertiary amino group, which has been widely used for Alzheimer's disease dementia. Donepezil hydrochloride is characterized by its solubility of 11 to 16 mg/mL in the 0.1 N hydrochloric acid solution and the 50 mM phosphate buffer, pH 6.0 and 0.1 mg/mL or less in the 50 mM phosphate buffer, pH 8.0, with the solubility in the 50 mM phosphate buffer, pH 6.8 being at least twice solubility in the 50 mM phosphate buffer, pH 8.0 and being not more than ½ solubility in the 50 mM phosphate buffer, pH 6.0.

There are no particular limitations on the dose of the anti-dementia drug or the salt thereof used in the present invention, but in the case of the acetylcholinesterase inhibitor, the dose is from 0.01 to 50 mg/day. More specifically, the dose of donepezil or a pharmacologically acceptable salt thereof is from 0.01 to 50 mg/day, preferably from 0.1 to 40 mg/day, more preferably from 1 to 30 mg/day, still more preferably from 5 to 25 mg/day. The dose of rivastigmine or a pharmacologically acceptable salt thereof is from 0.01 to 50 mg/day, preferably from 0.1 to 30 mg/day, more preferably from 1 to 20 mg/day, still more preferably from 1 to 15 mg/day. The dose of galantamine or a pharmacologically acceptable salt thereof is from 0.01 to 50 mg/day, preferably from 0.1 to 40 mg/day, more preferably from 1 to 30 mg/day, still more preferably from 2 to 25 mg/day.

Moreover, in the case of memantine or a pharmacologically acceptable salt thereof which acts as a NMDA receptor antagonist, the dose is from 0.5 to 100 mg/day, preferably from 1 to 100 mg/day, more preferably from 1 to 40 mg/day, still more preferably from 5 to 25 mg/day.

(High Molecular Weight Basic Substance)

The high molecular weight basic substance used in the present invention is a high molecular weight substance which exhibits basic properties when dissolved or suspended in water. For example, in a 2.5% aqueous solution or suspension the high molecular weight basic substance has a pH over 7.0, preferably a pH of 7.5 to 14.0, more preferably 8.0 to 14.0. Moreover, the high molecular weight basic substance used in the present invention can be formulated as a sustained-release base in the pharmaceutical composition according to the present invention, but may also be formulated for other purposes. In addition, the high molecular weight basic substance may also be insoluble in water or may also be a water-swelling substance or one which dissolves in water to form a gel. Examples of water-insoluble high molecular weight basic substances include cellulose ethers, cellulose esters and methacrylic acid-acrylic acid copolymers (trade name Eudragit, manufactured by Röhm GmbH & Co. KG, Darmstadt, Germany). Examples include, but are not limited to, cellulose alkyl ethers such as ethylcellulose (trade name Ethocel, manufactured by The Dow Chemical Company, U.S. and the like), ethyl methylcellulose, ethyl propylcellulose or isopropylcellulose, butylcellulose and the like; cellulose aralkyl ethers such as benzyl cellulose and the like; cellulose cyanoalkyl ethers such as cyanoethylcellulose and the like; cellulose organic acid esters such as cellulose acetate butyrate, cellulose acetate, cellulose propionate or cellulose butyrate, cellulose acetate propionate and the like; ethyl acrylate-methyl methacrylate copolymer (trade name Eudragit NE, manufactured by Röhm GmbH & Co. KG, Darmstadt, Germany) and the like. Examples of water-soluble or water-swelling high molecular weight basic substances include, but are not limited to, polyethylene oxide (trade name Polyox, manufactured by The Dow Chemical Company, U.S., molecular weight 100,000-7,000,000), low-substituted hydroxypropyl cellulose (trade name L-HPC, manufactured by Shin-Etsu Chemical, Japan) and the like. The high molecular weight basic substance can be singly contained or two or more may be contained in the pharmaceutical composition according to the present invention. The high molecular weight basic substance used in the present invention is preferably ethylcellulose, ethyl acrylate-methyl methacrylate copolymer (trade name Eudragit NE) or polyethylene oxide (trade name Polyox). More preferably, the high molecular weight basic substance is at least one of ethylcellulose and ethyl acrylate-methyl methacrylate copolymer. In a particularly preferred aspect, the high molecular weight basic substance is ethylcellulose. An amount of the high molecular weight basic substance in the pharmaceutical composition is not particularly limited and can be adjusted appropriately according to the purpose, such as controlling sustained-release characteristics of the drug or the like. There are no particular limitations on the mean particle size of the high molecular weight basic substance (the water-insoluble polymer substance) used in the present invention, but the mean particle size is preferably 0.1 to 100 μm, more preferably 1 to 50 μm, still more preferably 3 to 15 μm, most preferably 5 to 15 μm.

An amount of the high molecular weight basic substance in the matrix type sustained-release preparation is not particularly limited, but is generally 1 to 90% by weight, preferably 3 to 70% by weight, more preferably 5 to 50% by weight, still more preferably 5 to 35% by weight, based on 100% by weight of the pharmaceutical composition.

(Degradation Products)

Degradation products in the present invention are degradation products derived from the anti-dementia drug as a result of contact between the anti-dementia drug and the high molecular weight basic substance. It is presumed that the degradation products result from reactions of the amino group in the anti-dementia drug. For example, degradation products resulting from contact between donepezil hydrochloride and the high molecular weight basic substance can be detected by the ordinary means using liquid chromatography.

(High Molecular Weight Acidic Substance)

The high molecular weight acidic substance used in the present invention is a high molecular weight substance which exhibits acidity when dissolved or suspended in water, for example, with a 2.5% aqueous solution of the high molecular weight acidic substance exhibiting a pH of less than 7.0, preferably a pH of 1.0 to 6.5, more preferably a pH of 1.0 to 6.0. The high molecular weight acidic substance used in the present invention may also be insoluble in water or may also be a water-swelling substance or one which forms a gel when dissolved in water. The high molecular weight acidic substance used in the present invention is; for example, an enteric polymer substance. Examples of the enteric polymer substance include, but are not limited to, methacrylic acid-methyl methacrylate copolymer (Eudragit L100 (methacrylic acid copolymer, type A), Eudragit S100 (methacrylic acid copolymer, type B), which are manufactured by Röhm GmbH & Co. KG, Darmstadt, Germany), methacrylic acid-ethyl acrylate copolymer (Eudragit L100-55 (methacrylic acid copolymer, type C), Eudragit L30D-55 (methacrylic acid copolymer dispersion), which are manufactured by Röhm GmbH & Co. KG, Darmstadt, Germany), hydroxypropyl methylcellulose phthalate (HP-55, HP-50, which is manufactured by Shin-Etsu Chemical, Japan), hydroxypropyl methylcellulose acetate succinate (AQOAT, which is manufactured by Shin-Etsu Chemical, Japan), carboxymethyl ethylcellulose (CMEC, which is manufactured by Freund Corporation, Japan), phthalate acetate cellulose and the like. Examples of high molecular weight acidic substances which are water-swelling substances or form gels when dissolved in water as the high molecular weight acidic substance used in the present invention include, but are not limited to, alginic acid, pectin, carboxyvinyl polymer, carboxymethyl cellulose and the like. The high molecular weight acidic substance used in the present invention can be used singly or two or more can be contained in the pharmaceutical composition according to the present invention. The high molecular weight acidic substance used in the present invention is preferably an enteric polymer substance, and more preferably methacrylic acid-ethyl acrylate copolymer, methacrylic acid-methyl methacrylate copolymer, hydroxypropyl methylcellulose phthalate and hydroxypropyl methylcellulose acetate succinate, and still more preferably methacrylic acid-ethyl acrylate copolymer.

When used in a manufacturing process for the pharmaceutical composition, the high molecular weight acidic substance used in the present invention may be a commercial product of a powder or a granular type, or a suspension type which has been previously dispersed in a solvent, and these commercial products can be used as is or dispersed in water or an organic solvent. The smaller particle diameter of the high molecular weight acidic substance is suitable for the present invention, and it is preferably of the powder type. An example of the powder type includes Eudragit L100-55 in the case of methacrylic acid-ethyl acrylate copolymer. The particle diameter of the high molecular weight acidic substance used in the present invention is not particularly limited, but is preferably 0.05 to 100 μm, more preferably 0.05 to 70 μm, most preferably 0.05 to 50 μm.

Of the high molecular weight acidic substances, the enteric polymer substance is extremely useful because its stabilizing effect on the anti-dementia drug is not lost even when the enteric polymer substance is contained in large quantities in the pharmaceutical composition according to the present invention. Accordingly, there are no limitations on an amount of the high molecular weight acidic substance, but for example, the amount of the high molecular weight acidic substance is generally 0.1 to 90 parts by weight, preferably 1 to 70 parts by weight, more preferably 5 to 60 parts by weight, most preferably 10 to 50 parts by weight, based on 100 parts by weight of the pharmaceutical composition according to the present invention.

An amount of the enteric polymer in the pharmaceutical composition is not particularly limited, but is generally 5 to 90% by weight, preferably 8 to 70% by weight, more preferably 10 to 60% by weight, most preferably 15 to 50% by weight, based on 100% by weight of the pharmaceutical composition. A total amount of the water-insoluble polymer and the enteric polymer in the pharmaceutical composition is not particularly limited, but is generally 25 to 95% by weight, preferably 35 to 95% by weight, more preferably 40 to 90% by weight, still more preferably 35 to 90% by weight, most preferably 35 to 75% by weight, based on 100% by weight of the pharmaceutical composition.

A total amount of the high molecular weight basic substance (the water-insoluble polymer substance) and the high molecular weight acidic substances (the enteric polymer substance) in the pharmaceutical composition is not particularly limited, but is generally 25 to 95 parts by weight, preferably 35 to 95 parts by weight, still more preferably 35 to 90% by weight, most preferably 35 to 75% by weight, based on 100 parts by weight of the pharmaceutical composition.

(Low Molecular Weight Acidic Substance)

There are no particular limitations on the low molecular weight acidic substance used in the present invention as long as the pH of the solution is less than 4.5 when dissolved or suspended in water as a 2.5% aqueous solution or 2.5% suspension, and preferably a pH of 1.0 to 4.0, more preferably 1.0 to 3.5, still more preferably 1.0 to 3.0. Taken together with the anti-dementia drug, given the anti-dementia drug with a pH of 4.0 to 6.0 in a 2 to 5% aqueous solution or suspension, the pH of this aqueous solution minus the pH of a 2.5% aqueous solution or 2.5% suspension of the low molecular weight acidic substance is generally 0.05 to 5.5, preferably 0.5 to 5.5, more preferably 1.0 to 5.0, still more preferably 1.5 to 5.0.

Moreover, examples of the low molecular weight acidic substance used in the present invention, even if it has a basic functional group or the like in addition to an acidic functional group, include, but are not limited to, amino acids or ethylenediamine tetraacetic acid, as long as the pH of a 2.5% aqueous solution or 2.5% suspension is less than 4.5. The term "low molecular weight" used in the present invention refers to a molecular weight of 1000 or less, which excludes the high molecular weight acidic substance used in the present invention. Moreover, the low molecular weight acidic substance used in the present invention may be either water-soluble or water-insoluble, but is preferably a solid at room temperature and also preferably has the property of low volatility. Either one or two or more of the low molecular weight substances used in the present invention may be contained in the pharmaceutical composition.

There are no particular limitations on the low molecular weight acidic substance, but examples include, but are not limited to, organic acids, inorganic acids or acidic amino acids. Examples of organic acids include, but are not limited to, carboxylic acids such as acetic acid, benzoic acid, lauric acid, myristic acid, palmitic acid, stearic acid, oxalic acid, malonic acid, succinic acid, adipic acid, sebacic acid, fumaric acid, maleic acid, glycyrrhizic acid, glycyrrhetic acid, sorbic acid and the like; hydroxy acids such as glycolic acid, lactic acid, malic acid, tartaric acid, citric acid, sodium dihydrogen citrate, gluconic acid, salicylic acid and the like; sulfonic acids such as tosylic acid, mesylic acid and the like. Examples of inorganic acids include, but are not limited to, hydrochloric acid, sulfuric acid, boric acid, phosphoric acid, sodium dihydrogen phosphate, potassium dihydrogen phosphate and the like. Examples of acidic amino acids include, but are not limited to, aspartic acid, glutamic acid, glutamic acid hydrochloride, histidine hydrochloride and the like. Carboxylic acids, hydroxy acids, acidic amino acids and inorganic acids are preferable, and hydroxy acids, acidic amino acids and inorganic acids are more preferable. More specifically, preferable examples of the low molecular weight acidic substance used in the present invention include, but are not limited to, succinic acid, tartaric acid, citric acid, fumaric acid, maleic acid, malic acid, aspartic acid, glutamic acid, glutamic acid hydrochloride, hydrochloric acid or phosphoric acid, and succinic acid, tartaric acid, citric acid, malic acid, aspartic acid, glutamic acid, glutamic acid hydrochloride, hydrochloric acid or phosphoric acid are more preferable. Citric acid, aspartic acid and hydrochloric acid are still more preferable.

The effects of the present invention are obtained especially when the low molecular weight acidic substance is used in combination with the high molecular weight acidic substance. The amount of the high molecular weight acidic substance is not limited for purposes of stability, but may be adjusted from considerations of sustained-release characteristics. In this case, degradation products can be prevented or inhibited without any effect from the adjusted amount if the low molecular weight acidic substance is used in combination with the high molecular weight acidic substance. For example, the amount of the low molecular weight acidic substance is generally 0.05 to 4 parts by weight, preferably 0.1 to 3 parts by weight, more preferably 0.15 to 2 parts by weight, still more preferably 0.15 to 1.5 parts by weight, based on 100 parts by weight of the pharmaceutical composition according to the present invention.

(Anti-Oxidant)

There are no particular limitations on the anti-oxidant used in the present invention as long as the anti-oxidant is one which produces anti-oxidizing effects as it is oxidized, and it is preferable that the anti-oxidant itself be more easily oxidized than the anti-dementia drug having amino groups. Therefore, the anti-oxidant used in the present invention has a reducing effect. Examples of the anti-oxidant used in the present invention include, but are not limited to, ascorbic acids such as ascorbic acid, sodium ascorbate, erythorbic acid, sodium erythorbate, ascorbic acid palmitate, ascorbic acid glucoside and the like; sulfur-containing amino acids such as cysteine, cysteine hydrochloride, methionine and the like; sulfites such as sodium sulfite, sodium hydrogen sulfite and the like; catechol derivatives such as catechol, chlorogenic acid, caffeic acid, tyrosine and the like; hydroquinone derivatives such as dibutylhydroxytoluene, butylhydroxyanisol and the like; gallic acid derivatives such as gallic acid, gallic acid esters, tannic acid and the like; tocopherols such as dl-$\alpha$-tocopherol, d-$\alpha$-tocopherol, d-$\beta$-tocopherol, d-$\gamma$-tocopherol, d-$\delta$-tocopherol, d-$\alpha$-tocotrienol, d-$\beta$-tocotrienol, d-$\gamma$-tocotrienol, d-$\delta$-tocotrienol, mixtures thereof and the like; flavones such as rutin, quercetin, hesperidin and the like; and polyphenols such as catechin, epicatechin, gallocatechin, proanthocyanidin and the like. The ascorbic acids, sulfur-containing amino acids, hydroquinone derivatives and tocopherols are preferred. More preferred are the ascorbic acids or sulfur-containing amino acids. Particularly preferable are methionine, ascorbic acid or cysteine hydrochloride. The anti-oxidant used in the present invention may be either in free or salt form, but preferably when it is dissolved or suspended in water such aqueous solutions exhibits acidity. For example, ascorbic acid is more preferable than sodium ascorbate, and cysteine hydrochloride is preferred over cysteine. The anti-oxidant used in the present invention may be used singly, or two or more may be contained, or it can be used in combination with the low molecular weight acidic substance. The anti-oxidant used in the present invention can be either water-soluble or water-insoluble, but preferably it is a solid at room temperature and more preferably it has the property of low volatility.

There are no particular limitations on the ratios of the antioxidant to the drug which are used in the present invention, but for example, the oxidant can be generally 0.01 to 10 parts by weight, preferably 0.02 to 5 parts by weight, more preferably 0.05 to 2 parts by weight, based on 1 part by weight of the drug. There are no particular limitations on the amount of the anti-oxidant, which is generally 0.001 to 5 parts by weight, preferably 0.01 to 3 parts by weight, more preferably 0.1 to 2 parts by weight, still more preferably 0.15 to 1.5 parts by weight based 100 parts by weight by of the pharmaceutical composition according to the present invention.

(A Water-Soluble Sugar and/or a Water-Soluble Sugar Alcohol)

The pharmaceutical composition according to the present invention preferably also comprises a water-soluble sugar and/or a water-soluble sugar alcohol. There are no particular limitations on the water-soluble sugar and/or the water-soluble sugar alcohol. Examples of the water-soluble sugars include, but are not limited to, lactose, sucrose, glucose, dextrin, pullulan and the like. Examples of the water-soluble sugar alcohols include, but are not limited to, mannitol, erythritol, xylitol, sorbitol and the like, with lactose and mannitol being preferred. There are no particular limitations on the amount of the water-soluble sugar or the water-soluble sugar alcohol in the pharmaceutical composition according to the present invention, but the above amount is generally 3 to 70% by weight, preferably 5 to 60% by weight, more preferably 10 to 60% by weight, still more preferably 12 to 60% by weight, based on 100% by weight of the matrix type sustained-release preparation.

(Excipient)

The pharmaceutical composition according to the present invention comprises additives including various pharmaceutically acceptable carriers such as excipients, lubricants, binders and disintegrators as well as preservatives, colorants, sweeteners, plasticizers, film coatings and the like as necessary. Examples of excipients include, but are not limited to, starch, pregelatinized starch, crystalline cellulose, light anhydrous silicic acid, synthetic aluminum silicate, magnesium aluminate metasilicate and the like. Examples of lubricants include, but are not limited to, magnesium stearate (Mallinckrodt Baker, Inc. USA), calcium stearate (Merck KGaA, Darmstadt, Germany), talc, sodium stearyl fumarate and the like. Examples of binders include, but are not limited to, hydroxypropyl cellulose, methylcellulose, carboxymethyl cellulose sodium, hydroxypropyl methylcellulose, polyvinylpyrrolidone and the like. Examples of disintegrators include, but are not limited to, carboxymethyl cellulose, carboxymethyl cellulose calcium, croscarmellose sodium, carboxymethyl starch sodium, low-substituted hydroxypropyl cellulose and the like. Examples of preservatives include, but are not limited to, paraoxybenzoic acid esters, chlorobutanol, benzyl alcohol, phenethyl alcohol, dehydroacetic acid, sorbic acid and the like. Preferable examples of colorants include, but are not limited to, water-insoluble lake pigments, natural pigments (such as β-carotene, chlorophyll and iron oxide), yellow iron sesquioxide, red iron sesquioxide, black iron oxide and the like. Examples of sweeteners include, but are not limited to, sodium saccharin, dipotassium glycyrrhizate, aspartame, stevia and the like. Examples of plasticizers include, but are not limited to, glycerin fatty acid esters, triethyl citrate, propylene glycol, polyethylene glycol and the like. Examples of film coating bases include, but are not limited to, hydroxypropyl methylcellulose, hydroxypropyl cellulose and the like.

(Pharmaceutical Composition)

The pharmaceutical composition according to the present invention is not particularly limited as long as it is a composition in which an anti-dementia drug is stabilized, but preferably it is a composition with sustained-release properties or a sustained-release preparation, and more preferably it is a matrix type sustained-release preparation. There are also no particular limitations on the dosage form of the pharmaceutical composition according to the present invention, which can be used in any formulation including tablets, capsules, granules, fine granules, powder, ointment, injection, poultice, inhalant, jelly or the like. Preferably the dosage form is in a formulation suitable for oral administration such as tablets, capsules, granules, fine granules, jelly or the like, and more preferably it is in the form of tablets, capsules, granules or fine granules.

Moreover, the pharmaceutical composition according to the present invention is a pharmaceutical composition containing the anti-dementia drug, the high molecular weight basic substance and the high molecular weight acidic substance. There are no particular limitations on how the anti-dementia drug, high molecular weight basic substance and high molecular weight acidic substance are distributed in the pharmaceutical composition, and these ingredients can be mixed uniformly in the same phase of the pharmaceutical composition according to the present invention. Specifically, it is the pharmaceutical composition comprising a matrix containing a mixture of the anti-dementia drug, the high molecular weight basic substance and the high molecular weight acidic substance, and is, for example, a matrix type sustained-release preparation. The matrix of the present invention is one in which the drug and sustained-release base are uniformly mixed and molded or granulated. Of course, other additives may also be mixed in such matrices, or the matrix may be further covered with a coating layer containing a shading agent or a moisture-proofing agent or the like.

The drug and the high molecular weight basic substance may also be contained separately in adjacent phases in the pharmaceutical composition according to the present invention. Moreover, a phase containing the drug and a phase containing the high molecular weight basic substance, each may comprise a plurality of phases which are stacked in layers. In this case, the high molecular weight acidic substance can be contained in at least one phase of either of the phases. For example, the pharmaceutical composition according to the present invention may comprise a core containing the anti-dementia drug, which is covered with a coating layer containing the high molecular weight basic substance, with the high molecular weight acidic substance being mixed into at least one of the core and the coating layer and, for example, may be a sustained-release coated preparation. Note that there are no particular limitations on the core, which may be in the form of granules or tablets, or other form. Examples include tablets in which a coating containing the high molecular weight basic substance is coated directly on a core which is a uncoated tablet containing a mixture of both the drug and high molecular weight acidic substance, granules in which a coating containing the high molecular weight basic substance and high molecular weight acidic substance is coated directly on a core consisting of granules containing the drug, and stacked granules containing a layer in which the drug and the high molecular weight acidic substance are contained in core granules such as nonpareil or the like, and a layer containing the high molecular weight basic substance. Use is made of tablets or capsules containing stacked granules containing a layer containing the high molecular weight acidic substance and the high molecular weight basic substance in the core granules such as nonpareil or the like, and a layer containing the drug.

Moreover, the pharmaceutical composition according to the present invention may be a pharmaceutical composition in which a phase containing the high molecular weight acidic substance is placed between a phase containing the drug and a phase containing the high molecular weight basic substance so that the anti-dementia drug does not come into contact with the high molecular weight basic substance. Granules can also be formed by coating a core containing the drug with a mixture containing the high molecular weight acidic substance, and then covering the core with a coating layer containing the high molecular weight basic substance and the high molecular weight acidic substance.

(Method for Mixing the High Molecular Weight Acidic Substance)

Conventionally known operating methods (such as those described in the Japanese Pharmacopoeia, 14$^{th}$ Ed., General Rules for Preparations) can be used when containing the high molecular weight acidic substance in the pharmaceutical composition according to the present invention, either during the mixing step, granulating step, compression-molding step, coating step, packing step or any other step in manufacturing the pharmaceutical composition or during multiple steps. Although not limited to these, specific examples include (a) a method in which in a step of dry mixing or wet mixing the drug and the high molecular weight basic substance, the high molecular weight acidic substance is also added, (b) a method in which the high molecular weight acidic substance is suspended in the water or other binder used to wet-granulate a mixture of the drug and a water-insoluble polymer substance so as to add the high molecular weight acidic substance, (c) a method in which the high molecular weight acidic substance is added as a powder when dry-granulating a mixture of the drug and the water-insoluble polymer substance, (d) a method in which during the step of mixing and compression-molding granules containing the drug and granules containing the high molecular weight basic substance, the high molecular weight acidic substance is added as a powder, (e) a method of adding the high molecular weight acidic substance in advance to the coating liquid or the like for forming a coating layer when granules or tablets containing the drug are given a sugar coat or film coat containing the high molecular weight basic substance, and (f) a method of packing capsules with powders or granules of the high molecular weight acidic substance together with granules containing the drug and granules containing the high molecular weight basic substance. The high molecular weight acidic substance can preferably be added in at least one of the mixing step and the granulating step. More preferable is a method in which the high molecular weight acidic substance is added as a powder or as a solution or suspension to a mixture of the drug and the high molecular weight basic substance during at least one of the mixing step and the granulating step. In this way granules in which all ingredients which are uniformly mixed can be obtained by this method. Particularly preferable is a method in which the high molecular weight acidic substance as a powder is added to a mixture of the drug and the high molecular weight basic substance. Note that there are no particular limitations on the solvents used in the various manufacturing steps including wet mixing and preparation of the solution or suspension of the stabilizer, but examples of the solvent include alcohol, water or a mixture of the foregoing, preferably ethanol, water or the mixture of the foregoing.

(Composition Mixed with Low Molecular Weight Acidic Substance or the Like)

The pharmaceutical composition according to the present invention is a pharmaceutical composition containing a low molecular weight acidic substance in addition to the anti-dementia drug, the high molecular weight basic substance and the high molecular weight acidic substance. There are no limitations on how the low molecular weight acidic substance is mixed in the pharmaceutical composition, and for example, it can be mixed into a phase in which the drug, the high molecular weight basic substance and the high molecular weight acidic substance are uniformly mixed. When the drug and the high molecular weight basic substance are in different phases, the low molecular weight acidic substance can be mixed into at least one of those phases in the pharmaceutical composition according to the present invention. It can also be coated either independently or together with the high molecular weight acidic substance onto the matrix or the core in the pharmaceutical composition. Note that an anti-oxidant can also be mixed in the pharmaceutical composition in the same way as the low molecular weight acidic substance as described above. Of course, the anti-oxidant may be mixed together with the low molecular weight acidic substance or may be mixed in the pharmaceutical composition separately from the low molecular weight acidic substance.

(Method of Adding a Low Molecular Weight Acidic Substance or the Like)

As in the case of mixing the high molecular weight acidic substance, the low molecular weight acidic substance or the anti-oxidant can be mixed in the composition during any step or during multiple steps of manufacturing the pharmaceutical composition. The low molecular weight acidic substance can be mixed in the same step in which the high molecular weight acidic substance is added, or in a different step. The low molecular weight acidic substance or the anti-oxidant is preferably added during at least one of the mixing step and the granulating step in manufacturing the pharmaceutical composition. More preferably, the high molecular weight acidic substance and the low molecular weight acidic substance are added in at least one of the mixing step and the granulating step of manufacturing the pharmaceutical composition. Addition of the low molecular weight acidic substance or the anti-oxidant is not limited to these aspects and adding methods, and the low molecular weight acidic substance or the anti-oxidant may be added as a powder or dispersed in a solution or suspension or sprayed on. In this case, even if a plurality of the low molecular weight acidic substances, the anti-oxidants and the high molecular weight acidic substance are added in the same step, the addition methods may vary depending on the substance or they can all be added by the same method. For example, in the mixing step the high molecular weight acidic substance can be added as a powder while the low molecular weight acidic substance or anti-oxidant is added as a solution or suspension, or the high molecular weight acidic substance can be added as a powder in the mixing step while the low molecular weight acidic substance or anti-oxidant is added as a solution or suspension in the granulating step, but these examples are not limiting.

There are no particular limitations on the method of manufacturing the pharmaceutical composition according to the present invention as long as it comprises a step of mixing the high molecular weight acidic substance into the pharmaceutical composition. The pharmaceutical composition according to the present invention can be manufactured by a combination of the known operating methods (such as those described in the Japanese Pharmacopoeia, 14$^{th}$ Ed., General Rules for Preparations). Taking a solid oral preparation as an example, tablets can be formed by adding and mixing an excipient, disintegrator or the like with the drug, if necessary, adding a binder to form granules, and then adding a disintegrator, lubricant or the like as necessary. Granules can be produced in roughly the same way as tablets by extrusion granulation, or by coating nonpareil (core containing 75% sucrose (W/W) and 25% corn starch (W/W)) with a powder dispersion containing the drug and additives, while spraying with water or a solution (concentration about 0.5 to 70% (W/V)) containing a binder. In the case of capsules, gelatin, hydroxypropyl methylcellulose or other capsules can be filled with the drug together with an excipient. These pharmaceutical compositions can also be coated with a coating agent either alone or together with a shading agent or a low molecular weight acidic substance or an anti-oxidant of the present invention in order to mask flavors or impart the enteric or sustained-release properties or the like.

The pharmaceutical composition according to the present invention can be manufactured by the following methods. 130 g of donepezil hydrochloride (Eisai Co. Ltd.), 624 g of ethylcellulose (trade name Ethocel 10FP, Dow Chemical Company), 780 g of Eudragit 100-55 (Röhm GmbH & Co. KG) and 988 g of lactose are mixed in a granulator. Wet granulation is carried out by adding an aqueous solution of 52 g of hydroxypropyl cellulose (HPC-L; Nippon Soda Co., Ltd) dissolved in a suitable amount of purified water to the mixture. The resulting granules are heat-dried using a tray drier, and sieved to obtain the desirable granule size. After sieving, 1 g of magnesium stearate (Mallinckrodt Baker, Inc.) based on 99 g of granules is added and mixed, and a rotary tableting machine can then be used to form tablets with 8 mm in diameter containing 10 mg of donepezil hydrochloride based on 200 mg of the tablet. Using a coating apparatus, these tablets can then be coated with an aqueous film containing hydroxypropyl cellulose or the like as its main component.

Alternatively, the pharmaceutical composition according to the present invention can be manufactured by the following methods. 130 g of donepezil hydrochloride (Eisai Co. Ltd.), 624 g of ethylcellulose (trade name Ethocel 10FP, Dow Chemical Company), 780 g of Eudragit L100-55 (Röhm GmbH & Co. KG) and 975 g of lactose are mixed in a granulator. Wet granulation is carried out by adding an aqueous solution of 52 g of hydroxypropyl cellulose (HPC-L; Nippon Soda Co., Ltd) and 13 g of citric acid which are dissolved in a suitable amount of purified water to the mixture. The resulting granules are heat-dried using a tray drier, and sieved to obtain the desirable granule size. After sieving, 1 g of magnesium stearate (Mallinckrodt Baker, Inc.) based on 99 g of granules is added and mixed, and a rotary tableting machine can then be used to form tablets with 8 mm in diameter containing 10 mg of donepezil hydrochloride based on 200 mg of the tablet. Using a coating apparatus, these tablets can then be coated with an aqueous film containing hydroxypropyl cellulose or the like as its main component.

EXAMPLES

The present invention is explained in more detail below using examples, but the present invention is not limited thereto. The additives used in the pharmaceutical compositions were reagents commercially available or were in compliance with the official documents such as the Japanese Pharmacopoeia, the Japanese Pharmaceutical Excipients 2003 (JPE 2003), and the Japan Pharmaceutical Codex 1997 (JPC 1997).

Example 1

A suitable amount of purified water was added to and mixed with 300 mg of donepezil hydrochloride (Eisai Co. Ltd.), 375 mg of ethylcellulose (Ethocel 10FP, Dow Chemical Company), 1500 mg of Eudragit L100-55 (Röhm GmbH & Co. KG) and 795 mg of lactose, and the mixture was heat dried in a thermostatic chamber. 30 mg of magnesium stearate (Mallinckrodt Baker, Inc.) was added to and mixed with the dried granules. 200 mg of this mixture was taken and made into tablets with an Autograph AG5000A (Shimazu Corporation) to obtain tablets with 8 mm in diameter containing 20 mg of donepezil hydrochloride.

Example 2

A suitable amount of purified water was added to and mixed with 20 mg of donepezil hydrochloride (Eisai Co. Ltd.), 500 mg of Eudragit L100-55 (Röhm GmbH & Co. KG), 1000 mg of lactose and 500 mg of ethylcellulose (Ethocel 10FP, Dow Chemical Company), and the mixture was heat dried in a thermostatic chamber to obtain granules containing about 1% of donepezil hydrochloride based on the total weight of the granule.

Example 3

20 mg of citric acid dissolved in a suitable amount of purified water was added to and mixed with 20 mg of donepezil hydrochloride (Eisai Co. Ltd.), 500 mg of Eudragit L100-55 (Röhm GmbH & Co. KG), 1000 mg of lactose and 500 mg of ethylcellulose (Ethocel 10FP, Dow Chemical Company), and the mixture was heat dried in a thermostatic chamber to obtain granules containing about 1% of donepezil hydrochloride based on the total weight of the granule.

Example 4

20 mg of sodium dihydrogen citrate dissolved in a suitable amount of purified water was added to and mixed with 20 mg of donepezil hydrochloride (Eisai Co. Ltd.), 500 mg of Eudragit L100-55 (Röhm GmbH & Co. KG), 1000 mg of lactose and 500 mg of ethylcellulose (Ethocel 10FP, Dow Chemical Company), and the mixture was heat dried in a thermostatic chamber to obtain granules containing about 1% of donepezil hydrochloride based on the total weight of the granule.

Example 5

20 mg of aspartic acid dissolved in a suitable amount of purified water was added to and mixed with 20 mg of donepezil hydrochloride (Eisai Co. Ltd.), 500 mg of Eudragit L100-55 (Röhm GmbH & Co. KG), 1000 mg of lactose and 500 mg of ethylcellulose (Ethocel 10FP, Dow Chemical Company), and the mixture was heat dried in a thermostatic chamber to obtain granules containing about 1% of donepezil hydrochloride based on the total weight of the granule.

Example 6

20 mg of ascorbic acid dissolved in a suitable amount of purified water was added to and mixed with 20 mg of donepezil hydrochloride (Eisai Co. Ltd.), 500 mg of Eudragit L100-55 (Röhm GmbH & Co. KG), 1000 mg of lactose and 500 mg of ethylcellulose (Ethocel 10FP, Dow Chemical Company), and the mixture was heat dried in a thermostatic chamber to obtain granules containing about 1% of donepezil hydrochloride based on the total weight of the granule.

Example 7

20 mg of sodium ascorbate dissolved in a suitable amount of purified water was added to and mixed with 20 mg of donepezil hydrochloride (Eisai Co. Ltd.), 500 mg of Eudragit L100-55 (Röhm GmbH & Co. KG), 1000 mg of lactose and 500 mg of ethylcellulose (Ethocel 10FP, Dow Chemical Company), and the mixture was heat dried in a thermostatic chamber to obtain granules containing about 1% of donepezil hydrochloride based on the total weight of the granule.

Example 8

20 mg of cysteine dissolved in a suitable amount of purified water was added to and mixed with 20 mg of donepezil hydrochloride (Eisai Co. Ltd.), 500 mg of Eudragit L100-55 (Röhm GmbH & Co. KG), 1000 mg of lactose and 500 mg of ethylcellulose (Ethocel 10FP, Dow Chemical Company), and the mixture was heat dried in a thermostatic chamber to obtain granules containing about 1% of donepezil hydrochloride based on the total weight of the granule.

Example 9

20 mg of cysteine hydrochloride dissolved in a suitable amount of purified water was added to and mixed with 20 mg of donepezil hydrochloride (Eisai Co. Ltd.), 500 mg of Eudragit L100-55 (Röhm GmbH & Co. KG), 1000 mg of lactose and 500 mg of ethylcellulose (Ethocel 10FP, Dow Chemical Company), and the mixture was heat dried in a thermostatic chamber to obtain granules containing about 1% of donepezil hydrochloride based on the total weight of the granule.

Example 10

20 mg of methionine dissolved in a suitable amount of purified water was added to and mixed with 20 mg of donepezil hydrochloride (Eisai Co. Ltd.), 500 mg of Eudragit L100-55 (Röhm GmbH & Co. KG), 1000 mg of lactose and 500 mg of ethylcellulose (Ethocel 10FP, Dow Chemical Company), and the mixture was heat dried in a thermostatic chamber to obtain granules containing about 1% of donepezil hydrochloride based on the total weight of the granule.

Example 11

130 g of donepezil hydrochloride (Eisai Co. Ltd.), 312 g of ethylcellulose (Ethocel 10FP, Dow Chemical Company), 624 g of Eudragit L100-55 (Röhm GmbH & Co. KG) and 1456 g of lactose were mixed in a granulator. Wet granulation was carried out by adding an aqueous solution of 52 g of hydroxypropyl cellulose (HPC-L; Nippon Soda Co., Ltd) dissolved in a suitable amount of purified water to the mixture, and the resulting granules were heat dried using a tray drier, and sieved to obtain the desired granule size. After sieving, 1 g of magnesium stearate (Mallinckrodt Baker, Inc.) based on 99 g of granules was added and mixed, and a rotary tableting machine was used to form tablets with 8 mm in diameter containing 10 mg of donepezil hydrochloride in 200 mg of the tablet. Using Opadry Yellow (Japan Colorcon), these tablets were then given a water-soluble film coating (coating amount: 8 mg/tablet) containing hydroxypropyl methylcellulose as its main component, to obtain film-coated tablets.

Example 12

130 g of donepezil hydrochloride (Eisai Co. Ltd.), 624 g of ethylcellulose (Ethocel 10FP, Dow Chemical Company), 780 g of Eudragit L100-55 (Röhm GmbH & Co. KG) and 988 g of lactose were mixed in a granulator. Wet granulation was carried out by adding an aqueous solution of 52 g of hydroxypropyl cellulose (HPC-L; Nippon Soda Co., Ltd) dissolved in a suitable amount of purified water to the mixture, and the resulting granules were heat dried using a tray drier, and sieved to obtain the desired granule size. After sieving, 1 g of magnesium stearate (Mallinckrodt Baker, Inc.) based on 99 g of granules was added and mixed, and a rotary tableting machine was used to form tablets with 8 mm in diameter containing 10 mg of donepezil hydrochloride in 200 mg of the tablet. Using Opadry Yellow (Japan Colorcon), these tablets were then given a water-soluble film coating (coating amount: 8 mg/tablet) containing hydroxypropyl methylcellulose as its main component, to obtain film-coated tablets.

Example 13

130 g of donepezil hydrochloride (Eisai Co. Ltd.), 780 g of ethylcellulose (Ethocel 10FP, Dow Chemical Company), 858 g of Eudragit L100-55 (Röhm GmbH & Co. KG) and 754 g of lactose were mixed in a granulator. Wet granulation was carried out by adding an aqueous solution of 52 g of hydroxypropyl cellulose (HPC-L; Nippon Soda Co., Ltd) dissolved in a suitable amount of purified water to the mixture, and the resulting granules were heat dried using a tray drier, and sieved to obtain the desired granule size. After sieving, 1 g of magnesium stearate (Mallinckrodt Baker, Inc.) based on 99 g of granules was added and mixed, and a rotary tableting machine was used to form tablets with 8 mm in diameter containing 10 mg of donepezil hydrochloride in 200 mg of the tablet. Using Opadry Yellow (Japan Colorcon), these tablets were then given a water-soluble film coating (coating amount: 8 mg/tablet) containing hydroxypropyl methylcellulose as its main component, to obtain film-coated tablets.

Example 14

130 g of donepezil hydrochloride (Eisai Co. Ltd.), 832 g of ethylcellulose (Ethocel 10FP, Dow Chemical Company), 962 g of Eudragit L100-55 (Röhm GmbH & Co. KG) and 598 g of lactose were mixed in a granulator. Wet granulation was carried out by adding an aqueous solution of 52 g of hydroxypropyl cellulose (HPC-L; Nippon Soda Co., Ltd) dissolved in a suitable amount of purified water to the mixture, and the resulting granules were heat dried using a tray drier, and sieved to obtain the desired granule size. After sieving, 1 g of magnesium stearate (Mallinckrodt Baker, Inc.) based on 99 g of granules was added and mixed, and a rotary tableting machine was used to form tablets with 8 mm in diameter containing 10 mg of donepezil hydrochloride in 200 mg of the tablet. Using Opadry Yellow (Japan Colorcon), these tablets were then given a water-soluble film coating (coating amount: 8 mg/tablet) containing hydroxypropyl methylcellulose as its main component, to obtain film-coated tablets.

Example 15

3.5 g of donepezil hydrochloride (Eisai Co. Ltd.), 37.8 g of Ethocel 10FP (ethylcellulose, Dow Chemical Company), 22.4 g of Eudragit L100-55 (Röhm GmbH & Co. KG) and 73.5 g of lactose (Pharmatose 200M manufactured by DMV Corporation) were mixed in a granulator. Wet granulation was carried out by adding an aqueous solution of 2.8 g of hydroxypropyl cellulose (HPC-L; Nippon Soda Co., Ltd) dissolved in a suitable amount of purified water to the mixture, and the resulting granules were heat-dried in a tray drier, and sieved to obtain the desired granule size by a power mill. After sizing, 50 mg of calcium stearate (Merck KGaA, Germany) based on 5000 mg of granules was added and mixed, and an Autograph AG5000A (Shimazu Corporation) was used to make a compression-molded product with 8 mm in diameter containing 5 mg of donepezil hydrochloride in 202 mg of the product, with a compression pressure of 1200 Kgf.

Example 16

3.5 g of donepezil hydrochloride (Eisai Co. Ltd.), 37.8 g of Ethocel 10FP (ethylcellulose, Dow Chemical Company), 22.4 g of Eudragit L100-55 (Röhm GmbH & Co. KG) and 73.08 g of lactose (Pharmatose 200M manufactured by DMV Corporation) were mixed in a granulator. Wet granulation was carried out by adding an aqueous solution of 2.8 g of hydroxypropyl cellulose (HPC-L; Nippon Soda Co., Ltd) and 0.42 g of citric acid dissolved in a suitable amount of purified water to the mixture, and the resulting granules were heat-dried in a tray drier, and sieved to obtain the desired granule size by a power mill. After sizing, 50 mg of calcium stearate (Merck KGaA, Germany) based on 5000 mg of granules was added and mixed, and an Autograph AG5000A (Shimazu Corporation) was used to make a compression-molded product with 8 mm in diameter containing 5 mg of donepezil hydrochloride in 202 mg of the product, with a compression pressure of 1200 Kgf.

Example 17

3.5 g of donepezil hydrochloride (Eisai Co. Ltd.), 37.8 g of Ethocel 10FP (ethylcellulose, Dow Chemical Company), 22.4 g of Eudragit L100-55 (Röhm GmbH & Co. KG) and 73.5 g of lactose (Pharmatose 200M manufactured by DMV Corporation) were mixed in a granulator. Wet granulation was carried out by adding an aqueous solution of 2.8 g of hydroxypropyl cellulose (HPC-L; Nippon Soda Co., Ltd) dissolved in a suitable amount of purified water to the mixture, and the resulting granules were heat-dried in a tray drier, and sieved to obtain the desired granule size by a power mill. After sizing, 50 mg of magnesium stearate (Mallinckrodt Baker, Inc.) based on 5000 mg of granules was added and mixed, and an Autograph AG5000A (Shimazu Corporation) was used to make a compression-molded product with 8 mm in diameter containing 5 mg of donepezil hydrochloride in 202 mg of the product, with a compression pressure of 1200 Kgf.

Example 18

3.5 g of donepezil hydrochloride (Eisai Co. Ltd.), 37.8 g of Ethocel 10FP (ethylcellulose, Dow Chemical Company), 22.4 g of Eudragit L100-55 (Röhm GmbH & Co. KG) and 73.08 g of lactose (Pharmatose 200M manufactured by DMV Corporation) were mixed in a granulator. Wet granulation was carried out by adding an aqueous solution of 2.8 g of hydroxypropyl cellulose (HPC-L; Nippon Soda Co., Ltd) and 0.42 g of citric acid dissolved in a suitable amount of purified water to the mixture, and the resulting granules were heat-dried in a tray drier, and sieved to obtain the desired granule size by a power mill. After sizing, 50 mg of magnesium stearate (Mallinckrodt Baker, Inc.) based on 5000 mg of granules was added and mixed, and an Autograph AG5000A (Shimazu Corporation) was used to make a compression-molded product with 8 mm in diameter containing 5 mg of donepezil hydrochloride in 202 mg of the product, with a compression pressure of 1200 Kgf.

Example 19

980 g of donepezil hydrochloride (Eisai Co. Ltd.), 3780 g of Ethocel 10FP (ethylcellulose, Dow Chemical Company), 2660 g of Eudragit L100-55 (Röhm GmbH & Co. KG) and 6188 g of lactose were mixed in a granulator. Wet granulation was carried out by adding an aqueous solution of 300 g of hydroxypropyl cellulose (HPC-L; Nippon Soda Co., Ltd) dissolved in a suitable amount of purified water to the mixture, and the resulting granules were heat-dried in a fluidized-bed drier, and sieved to obtain the desired granule size. After sizing, 0.3 g of magnesium stearate (Mallinckrodt Baker, Inc.) based on 99.7 g of granules was added and mixed, and a rotary tabletting machine was used to form a tablet with 8 mm in diameter containing 14 mg of donepezil hydrochloride in 200 mg of the tablet. Opadry purple (Colorcon Japan Limited) was used to give the resulting tablet a water-soluble film coating containing hydroxypropyl methylcellulose as its main component (coating amount: 8 mg/tablet), resulting in film-coated tablet.

Example 20

1050 g of donepezil hydrochloride (Eisai Co. Ltd.), 3780 g of Ethocel 10FP (ethylcellulose, Dow Chemical Company), 2240 g of Eudragit L100-55 (Röhm GmbH & Co. KG) and 6538 g of lactose were mixed in a granulator. Wet granulation was carried out by adding an aqueous solution of 350 g of hydroxypropyl cellulose (HPC-L; Nippon Soda Co., Ltd) dissolved in a suitable amount of purified water to the mixture, and the resulting granules were heat-dried in a fluidized-bed drier, and sieved to obtain the desired granule size. After sizing, 0.3 g of magnesium stearate (Mallinckrodt Baker, Inc.) based on 99.7 g of granules was added and mixed, and a rotary tabletting machine was used to form a tablet with 8 mm in diameter containing 15 mg of donepezil hydrochloride in 200 mg of the tablet. Opadry purple (Colorcon Japan Limited) was used to give the resulting tablet a water-soluble film coating containing hydroxypropyl methylcellulose as its main component (coating amount: 8 mg/tablet), resulting in film-coated tablet.

Example 21

1400 g of donepezil hydrochloride, (Eisai Co. Ltd.), 3500 g of Ethocel 10FP (ethylcellulose, Dow Chemical Company), 2520 g of Eudragit L100-55 (Röhm GmbH & Co. KG) and 6118 g of lactose were mixed in a granulator. Wet granulation was carried out by adding an aqueous solution of 420 g of hydroxypropyl cellulose (HPC-L; Nippon Soda Co., Ltd) dissolved in a suitable amount of purified water to the mixture, and the resulting granules were heat-dried in a fluidized-bed drier, and sieved to obtain the desired granule size. After sizing, 0.3 g of magnesium stearate (Mallinckrodt Baker, Inc.) based on 99.7 g of granules was added and mixed, and a rotary tabletting machine was used to form a tablet with 8 mm in diameter containing 20 mg of donepezil hydrochloride in 200 mg of the tablet. Opadry red (Colorcon Japan Limited) was used to give the resulting tablet a water-soluble film coating containing hydroxypropyl methylcellulose as its main component (coating amount: 8 mg/tablet), resulting in film-coated tablet.

Example 22

1610 g of donepezil hydrochloride (Eisai Co. Ltd.), 3500 g of Ethocel 10FP (ethylcellulose, Dow Chemical Company), 2520 g of Eudragit L100-55 (Röhm GmbH & Co. KG) and 5908 g of lactose were mixed in a granulator. Wet granulation was carried out by adding an aqueous solution of 420 g of hydroxypropyl cellulose (HPC-L; Nippon Soda Co., Ltd) dissolved in a suitable amount of purified water to the mixture, and the resulting granules were heat-dried in a fluidized-bed drier, and sieved to obtain the desired granule size. After sizing, 0.3 g of magnesium stearate (Mallinckrodt Baker, Inc.) based on 99.7 g of granules was added and mixed, and a rotary tabletting machine was used to form a tablet with 8 mm in diameter containing 23 mg of donepezil hydrochloride in 200 mg of the tablet. Opadry red (Colorcon Japan Limited) was used to give the resulting tablet a water-soluble film coating containing hydroxypropyl methylcellulose as its main component (coating amount: 8 mg/tablet), resulting in film-coated tablet.

Example 23

1610 g of donepezil hydrochloride (Eisai Co. Ltd.), 3080 g of Ethocel 10FP (ethylcellulose, Dow Chemical Company), 2940 g of Eudragit L100-55 (Röhm GmbH & Co. KG) and 5908 g of lactose were mixed in a granulator. Wet granulation was carried out by adding an aqueous solution of 420 g of hydroxypropyl cellulose (HPC-L; Nippon Soda Co., Ltd) dissolved in a suitable amount of purified water to the mixture, and the resulting granules were heat-dried in a fluidized-bed drier, and sieved to obtain the desired granule size. After sizing, 0.3 g of magnesium stearate (Mallinckrodt Baker, Inc.) based on 99.7 g of granules was added and mixed, and a rotary tabletting machine was used to form a tablet with 8 mm in diameter containing 23 mg of donepezil hydrochloride in 200 mg of the tablet. Opadry red (Colorcon Japan Limited) was used to give the resulting tablet a water-soluble film coating containing hydroxypropyl methylcellulose as its main component (coating amount: 8 mg/tablet), resulting in film-coated tablet.

Examples 24 to 30

The film-coated tablets shown in Table 1 can be prepared according to the methods described above.

[Table 1]

TABLE 1

| NAME OF COMPONENT | VENDOR | EXAMPLE 24 | EXAMPLE 25 | EXAMPLE 26 | EXAMPLE 27 | EXAMPLE 28 | EXAMPLE 29 | EXAMPLE 30 |
|---|---|---|---|---|---|---|---|---|
| Donepezil•HCl | Eisai | 12 | 12 | 14 | 18 | 18 | 30 | 30 |
| Ethocel 10 FP | Dow Chemical | 54 | 54 | 48 | 54 | 44 | 50 | 44 |
| Eudragit L100-55 | Röhm | 32 | 38 | 44 | 38 | 42 | 36 | 42 |
| Lactose (Pharmatose 200M) | DMV International | 97.4 | 91.4 | 88.4 | 84.4 | 90.4 | 77.4 | 77.4 |
| HPC-L | Nippon Soda | 4 | 4 | 5 | 5 | 5 | 6 | 6 |
| Magnesium Stearate | Mallinckrodt | 0.6 | 0.6 | 0.6 | 0.6 | 0.6 | 0.6 | 0.6 |
| tablet total (mg) | | 200 | 200 | 200 | 200 | 200 | 200 | 200 |
| Opadry purple (mg/tablet) | Colorcon Japan | 8 | 8 | 8 | 8 | 8 | 8 | 8 |
| Film-coated total (mg) | | 208 | 208 | 208 | 208 | 208 | 208 | 208 |

Examples 31 to 34

In accordance with component amounts in Table 2 and 3, each component was mixed in a mortar. 200 mg of this mixture was taken and made into tablet using an Autograph AG5000A (Shimazu Corporation) to obtain a tablet (tablet weight: 200 mg) with 8 mm in diameter containing 20 mg of donepezil hydrochloride or 20 mg of memantine hydrochloride.

[Table 2]

TABLE 2

| NAME OF COMPONENT | VENDOR | EXAMPLE 31 |
|---|---|---|
| Donepezil•HCl | Eisai | 300 |
| Ethocel 10 FP | Dow Chemical | 750 |
| Eudragit L100 | Röhm | 1500 |
| LACTOSE (FlowLac 100) | Meggle | 420 |
| MAGNESIUM STEARATE | Mallinckrodt | 30 |
| Total (mg) | | 3000 |

[Table 3]

TABLE 3

| NAME OF COMPONENT | VENDOR | EXAMPLE 32 | EXAMPLE 33 | EXAMPLE 34 |
|---|---|---|---|---|
| Memantine•HCl | Lachema s.r.o | 300 | 300 | 300 |
| Ethocel 10 FP | Dow Chemical | 750 | 750 | 750 |
| Eudragit L100-55 | Röhm | 1500 | — | — |
| Eudragit L100 | Röhm | — | 1500 | — |
| AQOAT LF | SHIN-ETSU CHEMICAL | — | — | 1500 |
| LACTOSE (FlowLac 100) | Meggle | 420 | 420 | 420 |
| MAGNESIUM STEARATE | Mallinckrodt | 30 | 30 | 30 |
| Total (mg) | | 3000 | 3000 | 3000 |

Comparative Example 1

300 mg of donepezil hydrochloride (Eisai Co. Ltd.), 750 mg of ethylcellulose (Ethocel 10FP, Dow Chemical Company), 1920 mg of lactose and 30 mg of magnesium stearate (Mallinckrodt Baker, Inc.) were mixed in a mortar. 200 mg of this mixture was taken and made into tablets using an Autograph AG5000A (Shimazu Corporation) to obtain tablets with 8 mm in diameter containing 20 mg of donepezil hydrochloride.

Comparative Example 2

300 mg of donepezil hydrochloride (Eisai Co. Ltd.), 750 mg of ethylcellulose (Ethocel 10FP, Dow Chemical Company), 1620 mg of lactose, 300 mg of citric acid and 30 mg of magnesium stearate (Mallinckrodt Baker, Inc.) were mixed in a mortar. 200 mg of this mixture was taken and made into tablets using an Autograph AG5000A (Shimazu Corporation) to obtain tablets with 8 mm in diameter containing 20 mg of donepezil hydrochloride.

Comparative Example 3

A suitable amount of purified water was added to and mixed with 20 mg of donepezil hydrochloride (Eisai Co. Ltd.), 1500 mg of lactose and 500 mg of ethylcellulose (Ethocel 10FP, Dow Chemical Company), and the mixture was heat dried in a thermostatic chamber to obtain granules containing about 1% of donepezil hydrochloride based on the total weight of the granule.

Comparative Example 4

20 mg of disodium citrate dissolved in a suitable amount of purified water was added to and mixed with 20 mg of donepezil hydrochloride (Eisai Co. Ltd.), 500 mg of Eudragit L100-55 (Röhm GmbH & Co. KG), 1000 mg of lactose and 500 mg of ethylcellulose (Ethocel 10FP, Dow Chemical Company), and the mixture was heat dried in a thermostatic chamber to obtain granules containing about 1% of donepezil hydrochloride based on the total weight of the granule.

Comparative Example 5

20 mg of sodium citrate dissolved in a suitable amount of purified water was added to and mixed with 20 mg of donepezil hydrochloride (Eisai Co. Ltd.), 500 mg of Eudragit L100-55 (Röhm GmbH & Co. KG), 1000 mg of lactose and 500 mg of ethylcellulose (Ethocel 10FP, Dow Chemical Company), and the mixture was heat dried in a thermostatic chamber to obtain granules containing about 1% of donepezil hydrochloride based on the total weight of the granule.

Comparative Example 6

20 mg of sodium aspartate dissolved in a suitable amount of purified water was added to and mixed with 20 mg of donepezil hydrochloride (Eisai Co. Ltd.), 500 mg of Eudragit L100-55 (Röhm GmbH & Co. KG), 1000 mg of lactose and 500 mg of ethylcellulose (Ethocel 10FP, Dow Chemical Company), and the mixture was heat dried in a thermostatic chamber to obtain granules containing about 1% of donepezil hydrochloride based on the total weight of the granule.

Comparative Example 7

20 mg of glycine dissolved in a suitable amount of purified water was added to and mixed with 20 mg of donepezil hydrochloride (Eisai Co. Ltd.), 500 mg of Eudragit L100-55 (Röhm GmbH & Co. KG), 1000 mg of lactose and 500 mg of ethylcellulose (Ethocel 10FP, Dow Chemical Company), and the mixture was heat dried in a thermostatic chamber to obtain granules containing about 1% of donepezil hydrochloride based on the total weight of the granule.

Comparative Example 8

20 mg of disodium edetate dissolved in a suitable amount of purified water was added to and mixed with 20 mg of donepezil hydrochloride (Eisai Co. Ltd.), 500 mg of Eudragit L100-55 (Röhm GmbH & Co. KG), 1000 mg of lactose and 500 mg of ethylcellulose (Ethocel 10FP, Dow Chemical Company), and the mixture was heat dried in a thermostatic chamber to obtain granules containing about 1% of donepezil hydrochloride based on the total weight of the granule.

Comparative Example 9

A suitable amount of purified water was added to and mixed with 20 mg of donepezil hydrochloride (Eisai Co. Ltd.), 1000 mg of lactose and 1000 mg of ethylcellulose (Ethocel 10FP, Dow Chemical Company), and the mixture was heat dried in a thermostatic chamber to obtain granules containing about 1% of donepezil hydrochloride based on the total weight of the granule.

Comparative Example 10

A suitable amount of purified water was added to and mixed with 20 mg of donepezil hydrochloride (Eisai Co. Ltd.) and 2000 mg of lactose, and the mixture was heat dried in a thermostatic chamber to obtain granules containing about 1% of donepezil hydrochloride based on the total weight of the granule.

Comparative Example 11

A suitable amount of purified water was added to and mixed with 20 mg of donepezil hydrochloride (Eisai Co. Ltd.), 1500 mg of lactose and 500 mg of Eudragit L100-55 (Röhm GmbH & Co. KG), and the mixture was heat dried in a thermostatic chamber to obtain granules containing about 1% of donepezil hydrochloride based on the total weight of the granule.

Test Example 1

Tablets containing 10% donepezil hydrochloride from Example 1 and Comparative Examples 1 and 2 were stored for one week in an open (unsealed) thermostatic chamber at 60° C., 75% RH, and amounts of degradation products before and after storage were measured. The measurement of the degradation products was carried out by the following degradation product assay method 1.

(Degradation Product Assay Method 1)

The amounts of the degradation products were evaluated by HPLC using an ODS-A column (YMC Co. LTd.) with 4.6 mm* of an inner diameter and 75 mm of a length as the measurement column under conditions of column temperature 35° C., flow rate 1 ml/min, detection wavelength 271 nm. The composition of the mobile phase and the linear gradient conditions are shown in Table 4. The amounts of the degradation products were calculated as a percentage of total peak area using as a benchmark the peak of degradation products eluted near a relative retention time of 1.1 to 1.2 relative to the main drug peak.

Mobile phase A: water/acetonitrile/70% perchloric acid aqueous solution=899/100/1 mixture Mobile phase B: water/acetonitrile/70% perchloric acid aqueous solution=99/900/1 mixture

[Table 4]

TABLE 4

| min | MOBILE PHASE A | MOBILE PHASE B |
|---|---|---|
| 0.00 | 75% | 25% |
| 6.00 | 75% | 25% |
| 9.00 | 0% | 100% |
| 10.00 | 0% | 100% |
| 10.01 | 75% | 25% |
| 13.00 | 75% | 25% |

The amounts of the degradation products eluted near a relative retention time of 1.1 to 1.2 relative to donepezil are shown in Table 5 as the measurement results for Test Example 1. While 0.12% degradation products were observed with Comparative Example 1, no degradation products was observed with Example 1, which contained 50% Eudragit L100-55 as the high molecular weight acidic substance. Other degradation products were not observed in either Example 1 or Comparative Example 1. In the case of Comparative Example 2, which contained 10% each of the drug and citric acid, not only were 0.77% degradation products produced near a relative retention time of 1.1 to 1.2, but a variety of additional degradation products were produced, with the total of all degradation products amounting to about 13%. It appeared that mixing citric acid, which was effective for achieving photostability of donepezil in a 0.1% donepezil solution in Japanese Patent Application Laid-Open No. H11-106353 described in the Background Art, actually increased degradation products in the case of the thermal stability of donepezil hydrochloride in a tablet containing 10% of donepezil hydrochloride. Even when Eudragit L100-55 as the high molecular weight acidic substance was added to the composition at a high concentration of 50%, no degradation products were detected, confirming an improvement effect on thermal stability of donepezil hydrochloride in the pharmaceutical composition. This shows the thermal stability improving effect of the high molecular weight acidic substance in a composition containing both the anti-dementia drug and the high molecular weight basic substance.

[Table 5]

TABLE 5

| | NAME OF COMPONENT | EXAMPLE 1 | COMPARATIVE EXAMPLE 1 | COMPARATIVE EXAMPLE 2 |
|---|---|---|---|---|
| AMOUNT (mg) | DONEPEZIL HYDROCHLORIDE | 300 | 300 | 300 |
| | ETHYLCELLULOSE | 375 | 750 | 750 |
| | EUDRAGIT L100-55 | 1500 | — | — |
| | LACTOSE | 795 | 1920 | 1620 |
| | CITRIC ACID | — | — | 300 |
| | MAGNESIUM STEARATE | 30 | 30 | 30 |
| | TOTAL | 3000 | 3000 | 3000 |
| | DEGRADATION PRODUCTS (%) | <0.05 | 0.12 | 0.77 |

Test Example 2

Granules containing about 1% donepezil hydrochloride of Examples 2 and 3 and Comparative Example 3 were stored for 2 weeks in an open (unsealed) thermostatic chamber at 60° C., 75% RH, and amounts of degradation products before and after storage were measured. The measurement of the degradation products was carried out by the following degradation product assay method 2. The granules of Comparative Examples 9 through 11 were tested in the same way to investigate the effects of Test Example 1.
(Degradation Product Assay Method 2)

From Comparative Example 3 and Example 2 it was also confirmed that degradation products' were suppressed by the inclusion of about 25% of Eudragit L100-55 in the pharmaceutical composition. No degradation products were observed in Example 2 or in Example 3, which also included about 1% citric acid. This confirmed once again that the high molecular weight acidic substance has a suppressing effect on generation of degradation products resulting from the co-existence of the anti-dementia drug and the high molecular weight basic substance, and also has a combined effect with citric acid.

[Table 6]

TABLE 6

| | NAME OF COMPONENT | EXAMPLE 2 | EXAMPLE 3 | COMPARATIVE EXAMPLE 10 | COMPARATIVE EXAMPLE 11 | COMPARATIVE EXAMPLE 3 | COMPARATIVE EXAMPLE 9 |
|---|---|---|---|---|---|---|---|
| AMOUNT (mg) | DONEPEZIL HYDROCHLORIDE | 20 | 20 | 20 | 20 | 20 | 20 |
| | ETHYLCELLULOSE | 500 | 500 | — | — | 500 | 1000 |
| | EUDRAGIT L100-55 | 500 | 500 | — | 500 | — | — |
| | LACTOSE | 1000 | 1000 | 2000 | 1500 | 1500 | 1000 |
| | CITRIC ACID | — | 20 | — | — | — | — |
| | TOTAL | 2020 | 2040 | 2020 | 2020 | 2020 | 2020 |
| | DEGRADATION PRODUCTS (%) | 0.28 | <0.1 | <0.1 | <0.1 | 0.51 | 1.26 |

The amounts of the degradation products was evaluated by HPLC using an Inertsil ODS-2 column (GL Sciences) with 4.6 mm of an inner diameter and 150 mm of a length as the measurement column with a 646.6/350/1/2.4 mixture of water/acetonitrile/70% perchloric acid aqueous solution/sodium decanesulfonate under conditions of column temperature 35° C., flow rate 1.4 mL/min, detection wavelength 271 nm. The amounts of the degradation products were calculated as a percentage of total peak area using as a benchmark the peak of degradation products eluted near a relative retention time of 1.1 to 1.2 relative to the main drug peak.

The amounts of the degradation products eluted near a relative retention time of 1.1 to 1.2 relative to donepezil are shown in Table 6 as the measurement results for Test Example 2. The degradation products were not detected in the case of Comparative Examples 10 and 11, which did not contain ethylcellulose as the high molecular weight basic substance, but 0.51% degradation products was observed in the case of Comparative Example 3, which contained ethylcellulose. In the case of Comparative Example 9, which contained more ethylcellulose, 1.26% degradation products were observed. This confirmed degradation products resulting from the combined presence of donepezil hydrochloride and ethylcellulose.

Test Example 3

To verify the combined effect of Eudragit L100-55 and the low molecular weight acidic substance, granules mixed with citric acid or a salt thereof (Examples 3 and 4, Comparative Examples 4 and 5), an amino acid (Example 5, Comparative Examples 6 and 7) or the salt of edetic acid (Comparative Example 8) were stored for 2 weeks in an open (unsealed) thermostatic chamber at 60° C., 75% RH, and amounts of degradation products before and after storage were measured. The measurement of the degradation products was carried out by the degradation product assay method 2 described above. Moreover, pH of solutions of the additives studied in this test example (that is, Eudragit L100-55 in Example 2 and additives mixed in the amount of 20 mg in the other examples and comparative examples) dissolved or suspended in purified water at a concentration of 2.5% was also measured. The pH values of 2% and 5% aqueous solutions of donepezil hydrochloride were also measured as reference values.

Amounts of the degradation products eluted near a relative retention time of 1.1 to 1.2 relative to donepezil are shown in Table 7 as the measurement results for Test Example 3. The amounts of the degradation products was 0.51% in Comparative Example 3 but only 0.28% in Example 2, in which Eudragit L100-55 alone was contained to suppress the degradation products. Moreover, degradation products in Examples 3 through 5 in which the low molecular weight acidic substance of the present invention was mixed were not more than 0.51% of Comparative Example 3, confirming that the degradation products were suppressed by combined use of Eudragit L100-55 and the low molecular weight acidic substance. The degradation products were further suppressed in the case of Example 3, which contained citric acid, and of Example 5, which contained aspartic acid, as compared to Example 2, in which only Eudragit L100-55 was mixed, confirming the synergistic effect of the low molecular weight acidic substance and the high molecular weight acidic substance on the thermal stability of donepezil hydrochloride in the pharmaceutical composition containing ethylcellulose. The additives used in this test (additives mixed in amounts of 20 mg in the examples and the comparative examples) were then evaluated for pH (2.5% aqueous solution or suspension). FIG. 1 shows the relationship between pH of 2.5% aqueous solutions or suspensions of various additives and the degradation products after granules mixed with those additives had been stored for 2 weeks under open (unsealed) conditions at 60° C., 75% RH. At a pH of 4.5, the amount of the degradation products was roughly the same as in Comparative Example 3, but as the pH increased, the amount of degradation products increased. On the other hand, below pH 4.5, the lower the pH, the stronger the thermal stabilization effect and the more degradation products was suppressed. Since the pH of a 2% aqueous solution of donepezil hydrochloride is 5.0 and the pH of a 5% aqueous solution of donepezil hydrochloride is 4.8, stability was reduced in Comparative Examples 4 through 7 than in Comparative Example 3 because they contained the additives with higher pH values than that of the aqueous solution of donepezil hydrochloride.

[Table 7]

Test Example 4

To evaluate the combined effect of Eudragit L100-55 and an anti-oxidant, the granules containing about 1% donepezil hydrochloride of Examples 6 through 10 and Comparative Example 8, which also contained various anti-oxidants, were stored for 2 weeks in an open (unsealed) thermostatic chamber at 60C, 75% RH, and amounts of degradation products before and after storage was measured. The measurement of the degradation products was carried out according to the previously described degradation product assay method 2. Moreover, the pH values of solutions of the additives studied in this test example (the additives mixed in the amount of 20 mg in the examples and comparative examples) dissolved or suspended in purified water at a concentration of 2.5% were also measured.

The amounts of the degradation products eluted near a relative retention time of 1.1 to 1.2 relative to donepezil are shown in Table 8 as the measurement results for Test Example 4. A stabilization effect was observed in Examples 6 through 10, in which Eudragit L100-55 and the anti-oxidant were contained, with generation of the degradation products being suppressed more than in Comparative Example 3. In particular, no degradation products were detected in the examples which contained ascorbic acid or a sulfur-containing amino acid, indicating a synergistic effect with Eudragit L100-55. On the other hand, the same level of degradation products as in Comparative Example 3 (with no additive) was observed in Comparative Example 8, which contained the anti-oxidant without reduction reaction (pH 4.5, 2% aqueous solution), confirming that chelating anti-oxidants did not contribute to stability.

As with the additives of Test Example 3, FIG. 1 shows the relationship between the amounts of the degradation products in the storage tests for Examples 6 through 10, which contained the anti-oxidants with reducing effects, and the pH values of 2.5% aqueous solutions or suspensions. A compari-

TABLE 7

| | NAME OF COMPONENT | EXAMPLE 2 | EXAMPLE 3 | EXAMPLE 4 | COMPARATIVE EXAMPLE 4 | COMPARATIVE EXAMPLE 5 | EXAMPLE 5 | COMPARATIVE EXAMPLE 6 | COMPARATIVE EXAMPLE 7 | COMPARATIVE EXAMPLE 8 | COMPARATIVE EXAMPLE 3 |
|---|---|---|---|---|---|---|---|---|---|---|---|
| AMOUNT (mg) | DONEPEZIL HYDROCHLORIDE | 20 | 20 | 20 | 20 | 20 | 20 | 20 | 20 | 20 | 20 |
| | ETHYLCELLULOSE | 500 | 500 | 500 | 500 | 500 | 500 | 500 | 500 | 500 | 500 |
| | EUDRAGIT L100-55 | 500 | 500 | 500 | 500 | 500 | 500 | 500 | 500 | 500 | — |
| | LACTOSE | 1000 | 1000 | 1000 | 1000 | 1000 | 1000 | 1000 | 1000 | 1000 | 1500 |
| | CITRIC ACID | — | 20 | — | — | — | — | — | — | — | — |
| | SODIUM DIHYDROGEN CITRATE | — | — | 20 | — | — | — | — | — | — | — |
| | DISODIUM CITRATE | — | — | — | 20 | — | — | — | — | — | — |
| | SODIUM CITRATE | — | — | — | — | 20 | — | — | — | — | — |
| | ASPARTIC ACID | — | — | — | — | — | 20 | — | — | — | — |
| | SODIUM ASPARTATE | — | — | — | — | — | — | 20 | — | — | — |
| | GLYCINE | — | — | — | — | — | — | — | 20 | — | — |
| | DISODIUM EDETATE | — | — | — | — | — | — | — | — | 20 | — |
| | TOTAL | 2020 | 2040 | 2040 | 2040 | 2040 | 2040 | 2040 | 2040 | 2040 | 2020 |
| | DEGRADATION PRODUCTS (%) | 0.28 | <0.1 | 0.27 | 0.76 | 0.86 | 0.18 | 1.09 | 0.70 | 0.53 | 0.51 |
| | pH OF ADDITIVES (2.5% AQUEOUS SOLUTIONS OR SUSPENSIONS) | 3.4 | 2.0 | 3.7 | 5.2 | 8.3 | 3.0 | 6.8 | 6.2 | 4.5 | — | son with the results of Test Example 3 shows that the effects of these anti-oxidants are different from their effects as the low molecular weight acidic substances.
[Table 8]

Test Example 6

Tablets containing 5 mg of donepezil hydrochloride from Example 15, 16, 17 and 18 were stored for 2 weeks in an open

TABLE 8

| | NAME OF COMPONENT | EXAMPLE 2 | EXAMPLE 6 | EXAMPLE 7 | EXAMPLE 8 | EXAMPLE 9 | EXAMPLE 10 | COMPARATIVE EXAMPLE 8 | COMPARATIVE EXAMPLE 3 |
|---|---|---|---|---|---|---|---|---|---|
| AMOUNT (mg) | DONEPEZIL HYDROCHLORIDE | 20 | 20 | 20 | 20 | 20 | 20 | 20 | 20 |
| | ETHYLCELLULOSE | 500 | 500 | 500 | 500 | 500 | 500 | 500 | 500 |
| | EUDRAGIT L100-55 | 500 | 500 | 500 | 500 | 500 | 500 | 500 | — |
| | LACTOSE | 1000 | 1000 | 1000 | 1000 | 1000 | 1000 | 1000 | 1500 |
| | CITRIC ACID | — | — | — | — | — | — | — | — |
| | ASCORBIC ACID | — | 20 | — | — | — | — | — | — |
| | SODIUM ASCORBATE | — | — | 20 | — | — | — | — | — |
| | CYSTEINE | — | — | — | 20 | — | — | — | — |
| | CYSTEINE HYDROCHLORIDE | — | — | — | — | 20 | — | — | — |
| | METHIONINE | — | — | — | — | — | 20 | — | — |
| | DISODIUM EDETATE | — | — | — | — | — | — | 20 | — |
| | TOTAL | 2020 | 2040 | 2040 | 2020 | 2040 | 2040 | 2040 | 2020 |
| | DEGRADATION PRODUCTS (%) | 0.28 | <0.1 | 0.30 | <0.1 | <0.1 | <0.1 | 0.53 | 0.51 |
| | pH OF ADDITIVES (2.5% AQUEOUS SOLUTIONS OR SUSPENSIONS) | 3.4 | 2.6 | 7.5 | 5.1 | 1.5 | 5.9 | 4.5 | — |

Test Example 5

The pH values of the high molecular weight acidic substances and the high molecular weight basic substances used in the present invention were measured in 2.5% aqueous solution or suspension. The pH values of 2% and 5% aqueous solutions of donepezil hydrochloride and a 2.5% aqueous solution of lactose were measured as reference values. The results are shown in Table 9.
[Table 9]

(unsealed) thermostatic chamber at 60° C., 75% RH, and amounts of degradation products before and after storage were measured. The measurement of the degradation products was carried out by the degradation product assay method 2 described above.

The amounts of the degradation products after storage at 60° C., 75% RH, which were eluted near a relative retention time of 1.1 to 1.2 relative to donepezil are shown in Table 10 as the measurement results of Test Example 6. As can be seen from Table 10, it was confirmed in Examples 15, 16, 17 and 18

TABLE 9

| NAME OF COMPONENT | TRADE NAME | VENDOR | pH |
|---|---|---|---|
| HYDROXYPROPYL METHYLCELLULOSE ACETATE SUCCINATE | AQOAT LF | SHIN-ETSU CHEMICAL | 3.9 |
| HYDROXYPROPYL METHYLCELLULOSE PHTHALATE | HPMCP HP-55S | SHIN-ETSU CHEMICAL | 3.3 |
| CARBOXYVINYL POLYMER | Carbopol 71G | Noveon | 3.1 |
| METHACRYLIC ACID-METHYL METHACRYLATE COPOLYMER | EudragitL100 | Röhm | 3.3 |
| METHACRYLIC ACID-METHYL METHACRYLATE COPOLYMER | EudragitS100 | Röhm | 3.2 |
| ETHYL ACRYLATE-METHYL METHACRYLATE COPOLYMER | EudragitNE30D | Röhm | 8.6 |
| POLYETHYLENE OXIDE | POLYOX WSR301 | Dow Chemical Company | 9.3 |
| ETHYLCELLULOSE | Ethocel 7FP | Dow Chemical Company | 9.4 |
| ETHYLCELLULOSE | Ethocel 10FP | Dow Chemical Company | 9.2 |
| ETHYLCELLULOSE | Ethocel 10 | Dow Chemical Company | 8.6 |
| ETHYLCELLULOSE | Ethocel 100FP | Dow Chemical Company | 8.1 |
| LACTOSE | FlowLac100 | Meggle | 5.5 |
| DONEPEZIL HYDROCHLORIDE (2% AQUEOUS SOLUTION) | — | EISAI | 5.0 |
| DONEPEZIL HYDROCHLORIDE (5% AQUEOUS SOLUTION) | — | EISAI | 4.8 | that the amounts of the degradation products could be inhibited to less than 0.5% based on the content of donepezil hydrochloride under stress conditions.

[Table 10]

TABLE 10

| | NAME OF COMPONENT | EXAMPLE 15 | EXAMPLE 16 | EXAMPLE 17 | EXAMPLE 18 |
|---|---|---|---|---|---|
| AMOUNT (mg) | DONEPEZIL HYDROCHLORIDE | 5 | 5 | 5 | 5 |
| | ETHYLCELLULOSE | 54 | 54 | 54 | 54 |
| | EUDRAGIT L100-55 | 32 | 32 | 32 | 32 |
| | LACTOSE | 105 | 104.4 | 105 | 104.4 |
| | HPC-L | 4 | 4 | 4 | 4 |
| | CITRIC ACID | — | 0.6 | — | 0.6 |
| | CALCIUM STEARATE | 2 | 2 | — | — |
| | MAGNESIUM STEARATE | — | — | 2 | 2 |
| | TOTAL | 202 | 202 | 202 | 202 |
| | DEGRADATION PRODUCTS (%) | 0.20 | 0.15 | 0.33 | 0.26 |

Test Example 7

The Stability tests were carried out using the tablets obtained in Examples 11, 12 and 14. In each of examples 11, 12 and 14, 50 tablets was filled into a bottle made of high-density polyethylene, and the bottle was sealed by an aluminum sheet. The bottle was also sealed by a screw cap made of polypropylene. After storing in a thermostatic chamber at 5° C. and 40° C., 75% RH, amounts of degradation products after and before storage were measured by use of degradation product assay method 2 described above.

The amounts of the degradation products after storage at 40° C., 75% RH, which were eluted near a relative retention time of 1.1 to 1.2 relative to donepezil are shown in Table 11 as the measurement results of Test Example 7. As can be seen from Table 11, it was confirmed in Examples 11, 12 and 14 that the amounts of the degradation products could be inhibited to less than 0.5% based on the content of donepezil hydrochloride. According to the Guideline of International Conference of Harmonization, in the case where the maximum dose of the drug substance per a day is from 10 mg to 100 mg, the threshold does of impurities necessary to confirm the safety of is less than 0.5% based on the drug substance, or is less than 200 μg as a total intake per a day. Moreover, it can be said that three years (at room temperature) can be warranted, which is the general guarantee period of the medical goods, if the quality of the drugs and medicines can be ensured at the storage under the conditions of 40%, 75% RH for six months. Note that amounts of degradation products from the tablets obtained in each of Examples 11, 12 and 14 was less than 0.05% based on donepezil hydrochloride, which is lower than detection limit for impurities.

According to the results of Test Example 7, it was confirmed that the present invention provides useful solutions for quality improvement of the pharmaceutical composition containing donepezil hydrochloride.

[Table 11]

TABLE 11

| | INITIAL | AFTER ONE MONTH | AFTER THREE MONTHS | AFTER SIX MONTHS |
|---|---|---|---|---|
| EXAMPLE 11 | NSL | 0.06% | 0.10% | 0.15% |
| EXAMPLE 12 | NSL | 0.09% | 0.18% | 0.28% |
| EXAMPLE 14 | NSL | 0.12% | 0.22% | 0.37% |

NSL means not more than 0.05%

INDUSTRIAL APPLICABILITY

According to the present invention, in the pharmaceutical composition containing an anti-dementia drug and a sustained-release base, a method is provided for preventing or inhibiting degradation products due to the contact of the anti-dementia drug with the sustained-release base, namely the present invention can provide a method for stabilizing the anti-dementia drug in the pharmaceutical composition. Moreover, because the pharmaceutical composition according to the present invention is of high quality and highly suitable for compliance, the present invention provide pharmaceutical products, particularly anti-dementia drugs, which can be taken without worry and with less burden on patients and their caregivers. The present invention also provides a simple method for manufacturing the pharmaceutical composition in which sustained-release characteristics are controlled and the anti-dementia drug is stabilized without the use of specialized coating techniques or manufacturing equipment.

The invention claimed is:

1. A pharmaceutical composition comprising donepezil or a pharmaceutically acceptable salt thereof, a water-insoluble high molecular weight basic substance, a high molecular weight acidic substance for stabilizing donepezil or a pharmaceutically acceptable salt thereof, and a water-soluble sugar or sugar alcohol in an oral matrix type sustained-release composition, wherein the water-insoluble high molecular weight basic substance is ethylcellulose in an amount of 12 to 32 percent by weight and the high molecular weight acidic substance is methacrylic acid-ethyl acrylate copolymer in an amount of 15.8 to 37 percent by weight.

2. The pharmaceutical composition according to claim 1, wherein the water-soluble sugar or sugar alcohol is lactose.

* * * * *

UNITED STATES PATENT AND TRADEMARK OFFICE
CERTIFICATE OF CORRECTION

PATENT NO. : 8,481,565 B2
APPLICATION NO. : 11/793722
DATED : July 9, 2013
INVENTOR(S) : Ueki et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 467 days.

Signed and Sealed this
Twelfth Day of May, 2015

Michelle K. Lee
*Director of the United States Patent and Trademark Office*